US008216854B2

(12) United States Patent
Ballerstadt et al.

(10) Patent No.: US 8,216,854 B2
(45) Date of Patent: Jul. 10, 2012

(54) DEVICE AND METHOD FOR MEASURING ANALYTES

(75) Inventors: Ralph Ballerstadt, Portland, OR (US); Roger McNichols, Pearland, TX (US); Ashok Gowda, Houston, TX (US)

(73) Assignee: BioTex, Inc., Houston, TX (US)

( * ) Notice: Subject to any disclaimer, the term of this patent is extended or adjusted under 35 U.S.C. 154(b) by 733 days.

(21) Appl. No.: 11/591,065

(22) Filed: Nov. 1, 2006

(65) Prior Publication Data

US 2007/0122829 A1  May 31, 2007

Related U.S. Application Data

(63) Continuation-in-part of application No. 10/735,153, filed on Dec. 12, 2003, now Pat. No. 7,166,458.

(60) Provisional application No. 60/438,490, filed on Jan. 7, 2003.

(51) Int. Cl.
*G01N 33/543* (2006.01)
(52) U.S. Cl. ........ 436/518; 436/528; 436/535; 436/164; 436/172; 435/7.1; 435/283.1; 435/287.1; 435/288.7; 422/50; 422/400; 422/68.1; 422/82.05; 422/82.08

(58) Field of Classification Search .......... 436/518, 436/528, 535, 164, 172; 435/7.1, 283.1, 435/287.1, 288.7; 422/50, 400, 68.1, 82.05, 422/82.08
See application file for complete search history.

(56) References Cited

U.S. PATENT DOCUMENTS

| 5,143,066 | A  | * | 9/1992  | Komives et al.   | 600/317 |
| 6,040,194 | A  | * | 3/2000  | Chick et al.     | 436/501 |
| 6,828,104 | B2 | * | 12/2004 | Lipshutz et al.  | 435/6   |
| 7,037,729 | B2 | * | 5/2006  | Nie et al.       | 436/535 |
| 2002/0197724 | A1 | * | 12/2002 | Noronha et al. | 436/95  |
| 2003/0059811 | A1 | * | 3/2003  | Djaballah et al. | 435/6   |

OTHER PUBLICATIONS

Russell et al., A Fluorscence Based Glucose Biosensor Using Concanavalin A and Dextran Encapsulated in a Poly(ethylene glycol) Hydrogel, 1999, Analytical Chemistry, vol. 71, pp. 3126-3132.*

* cited by examiner

*Primary Examiner* — Melanie J Yu
(74) *Attorney, Agent, or Firm* — Nancy N. Quan

(57) ABSTRACT

The present invention is directed to a system, device and method for measuring the concentration of an analyte in a fluid or matrix. A thermodynamically stabilized analyte binding ligand for use in the system, device and method is disclosed. The thermodynamically stabilized analyte binding ligand is resistant to degradation at physiological temperatures and its use within the device provides a minimally invasive sensor for monitoring the concentration of an analyte in a fluid or matrix as are present in the body of an animal.

51 Claims, 17 Drawing Sheets

Figure 1)

Figure 4) Arrangements of carrier entity

Figure 10 (see sketch Figure 1)

DEVICE AND METHOD FOR MEASURING ANALYTES

FIELD OF THE INVENTION

The field of the invention relates generally to devices, systems, and methods for the detection of analytes and more particularly to devices, systems, and methods using affinity-based sensor components.

BACKGROUND OF THE INVENTION

Glucose-monitoring methods and devices involve a variety of physico-chemical transduction principles including optical, amperometric to viscometric techniques. Currently, the most common method of blood glucose sensing is based on an electro-enzymatic sensing. This approach requires blood to be drawn and tested and often requires a finger stick to draw blood each time a reading is needed. This methodology is often time-consuming and can be painful. Minimally invasive approaches based on needle-type sensors (e.g. glucose-oxidase) have been investigated. While these approaches are less painful, the measurement of glucose in interstitial fluid has well-known limitations (oxygen dependence, diffusion-controlled). For example, since signal formation in enzyme sensors depends on the rate of glucose consumption, any process that may affect mass transport of glucose from tissue to sensor (e.g. by protein and cell depositions on membrane, or by fibrotic capsule formation) compromises the accuracy and stability of the glucose measurement.

Temperature-stable devices for glucose sensing are important to treatments and control of diabetes. Diabetes is a chronic disease characterized by a disorder of the metabolism of insulin, carbohydrate, fat, and protein, as well as in the structure and function of blood vessels. Diabetes is currently the leading cause of death in the USA and other countries. Estimates indicate that diabetes has reached epidemic proportions worldwide, with between 5 and 10% of the world population affected. Diabetes is expected to become the primary disease worldwide in the future. Intensive management of blood sugars through frequent monitoring is effective to prevent, or at least manage, the progression of diabetic complications such as kidney failure, heart disease, gangrene, and blindness. Maintaining blood glucose levels near normal levels is typically achieved by frequently monitoring blood glucose levels.

Accurate quantitative blood sugar analysis depends, in part, on the monitoring conditions such as sugar composition, buffer strength and pH. Temperatures ranging from 30° C. to 45° C. are also a common feature of many sugar-monitoring applications. At these temperatures, however, many biomolecules, such as proteins, become extremely unstable and prone to denaturation within a short period of time. Any technology involving sugar-specific receptor molecules which is intended to be used for monitoring sugar levels over long periods of time such as several days, weeks or even months, needs to generate a stable output, ensuring good reproducibility and minimal re-calibration requirement. Long-term continuous glucose monitoring in bioreactors or in patients with diabetes mellitus necessitates a heat-stable output, since the temperature is around 37° C. There is a need for new methodologies and devices which provide functional stability during continuous sugar detection at elevated temperatures over a long period of time.

BRIEF SUMMARY OF THE INVENTION

An analyte sensing device, system, and method are provided involving an analyte sensing component that includes a thermodynamically stabilized analyte binding ligand.

The foregoing has outlined rather broadly the features and technical advantages of a number of embodiments of the present invention in order that the detailed description of the present invention that follows may be better understood. Additional features and advantages of the invention will be described hereinafter.

DETAILED DESCRIPTION OF THE INVENTION

Figure 1:
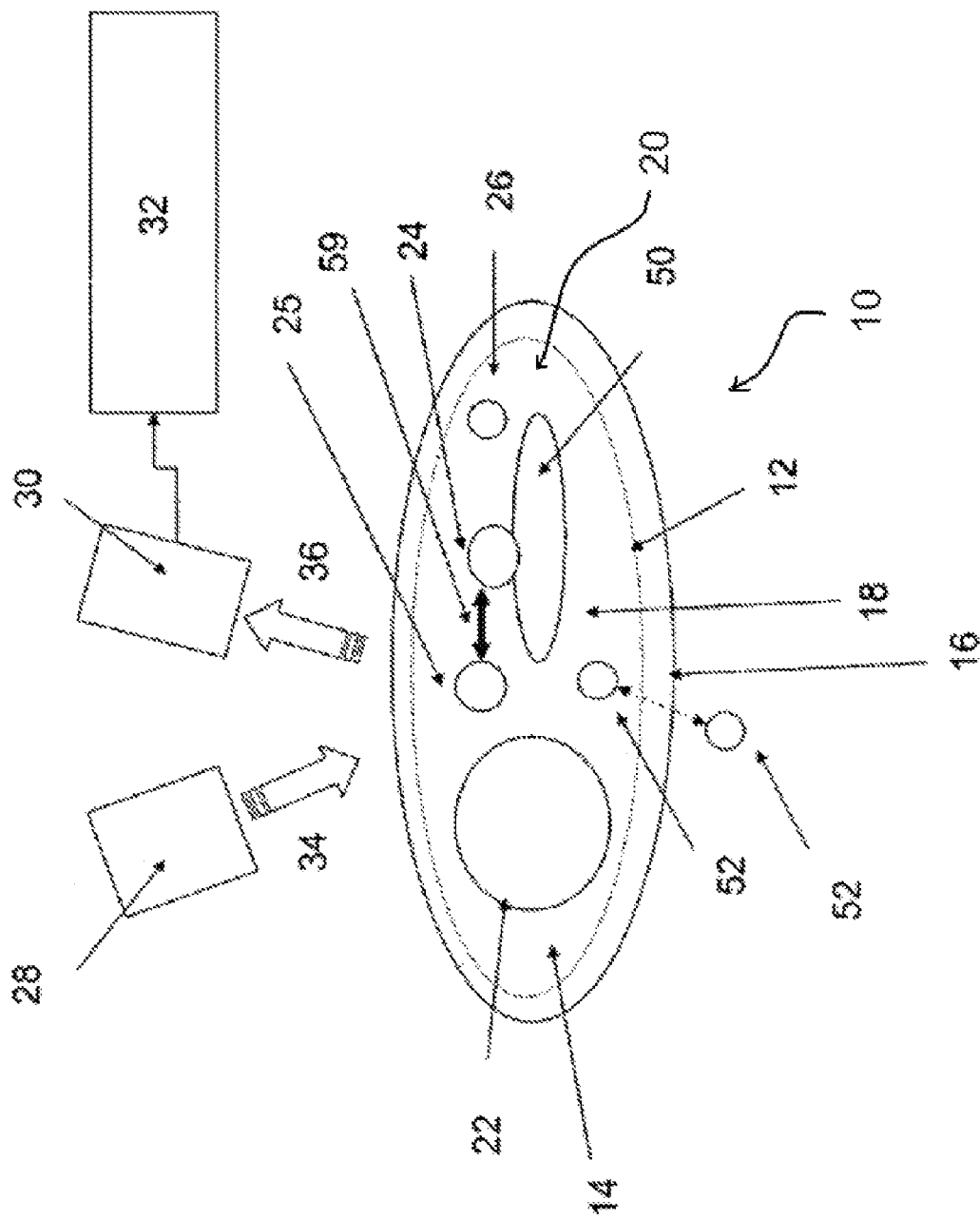
FIG. 1 shows an analyte sensing system.

A system, a device and a method for measuring the concentration of an analyte (e.g. glucose) in a biological fluid or tissue (e.g. the fluid in a bioreactor, food or agricultural product, or animal body) are disclosed. The system, device and method may be used to measure the concentration of analytes other than glucose, including but not limited to, such as drugs, hormones, peptides or other blood sugars (mannose, galactose).

The present analyte sensing device includes an analyte sensing component. The analyte sensing component is stabilized by a molecular entity in order to resist temperature-induced degradation of the analyte binding ligand. The analyte sensing component may include a plurality of reporting moieties and modulating moieties that are in contact with the biological fluid or tissue matrix and are capable of converting radiation of one or more different wavelengths. The ability to sense analytes at temperatures of 30° C. or higher over a long period of time is also disclosed. The conversion efficiency is at least partially dependent on the concentration of analyte within the fluid or matrix.

Exemplary sensing applications and corresponding binding ligand/analyte analog pairs are listed in Table I. Table 1 is not intended to be limiting and alternative combinations of disease/therapy, analyte, analyte binding ligand, molecular entity, and analyte analog are contemplated, for example as described in more detail in the description which follows.

contained in the analyte binding ligand. The molecular entity may be a molecular linkage bonded to the analyte binding ligand.

The molecular entity may be arranged in a fixed relationship with analyte binding ligand 22 for the purpose of thermodynamic stabilization of analyte binding ligand. The thermodynamic stabilization may be evidenced by stabilization from degradation at higher temperatures. Higher temperatures include from about 30° C. to about 50° C. The purpose of the molecular entity is to retain functional stability of analye binding ligand 22. The fixed relationship may be a fixed spatial relationship.

TABLE I

Exemplary assay systems for in vivo monitoring.

| Disease/Therapy | Analyte | Analyte Binding Ligand | Molecular Entity | Analyte Analogue |
|---|---|---|---|---|
| Diabetes mellitus | Glucose | Immobilized glucose-specific lectins (e.g. *Lens culinaris* lectin, *Pisum sativum* lectin, *Vicia faba* lectin, Concanavalin A) | Chemical linker; section of recombinant ConA, engineered ConA, or synthetic lectin analogues (MIP, Aptamer) | Glucose- or mannosylated albumin (or other protein), dendrimer |
| Hormone Treatment | Steroid (e.g. Hydrocortisone.) | Immobilized natural steroid-specific receptors, or antibody, Imprinted Polymers), Aptamer | Chemical linker; section of recombinant or engineered receptor, or synthetic receptor analogue (MIP, Aptamer) | Steroid-modified dextran, albumin, dendrimer |
| Chemotherapy | Chemotherapeutic drugs (chlorambucil, methotrexate, melphalan) | Immobilized Antibodies, | Chemical linker; section of recombinant or engineered antibodies, or synthetic antibody analogue (MIP, Aptamer) | Drug-modified polymer (dextran, dendrimer) |

Referring now to FIG. 1, analyte sensing device 10 may include analyte sensing component 12 disposed within housing 14. Housing 14 may include an impenetrable portion 16 and a semipermiable portion 18. Analyte sensing component 12 may include a macroporous hydrogel matrix 20, an analyte binding ligand 22, and first reporting moiety 24, and a modulating moiety 25. Analyte sensing component may further include second reporting moiety 26. Analyte sensing device 10 may be part of an analyte sensing system that includes radiation providing unit 28 and radiation detecting unit 30. The analyte sensing system may further include signal analyzer 32. Radiation providing unit may emit transmitted radiation 34 that is converted by analyte sensing component 12 to radiation detected at radiation detecting unit 30 as detected radiation 36. Analyte sensing component may include analyte analyte analog 50 capable of binding to analyte binding ligand 22. First reporting moiety 24 and modulating moiety 25 may be selected and arranged such that detected radiation 36 is dependent on the concentration of analyte 52 within housing 14. Further, analyte 52 may enter and exit analyte sensing component 12 through semipermiable portion 18. Thus, analyte sensing component 12 may sense the concentration of analyte 52 within housing 14. This concentration is in turn indicative of the concentration of analyte 52 in the environment containing analyte sensing device 10.

Analyte Binding Ligand

Analyte binding ligand 22 may be an analyte binding ligand which is stabilized from denaturation at higher temperatures. The analyte binding ligand 22 may contain or be bonded to a molecular entity to stabilize the analyte binding ligand. The molecular entity may be a molecule or monomer Analyte binding ligand 22 may be an analyte binding ligand derivatized by protein engineering; analyte binding ligand 22 may be a analyte binding ligand derivatized by genetic engineering; the molecular entity may be a chemical crosslinker for immobilizing the analyte binding ligand to a matrix; and the molecular entity may be a synthetic receptor.

Figure 2:
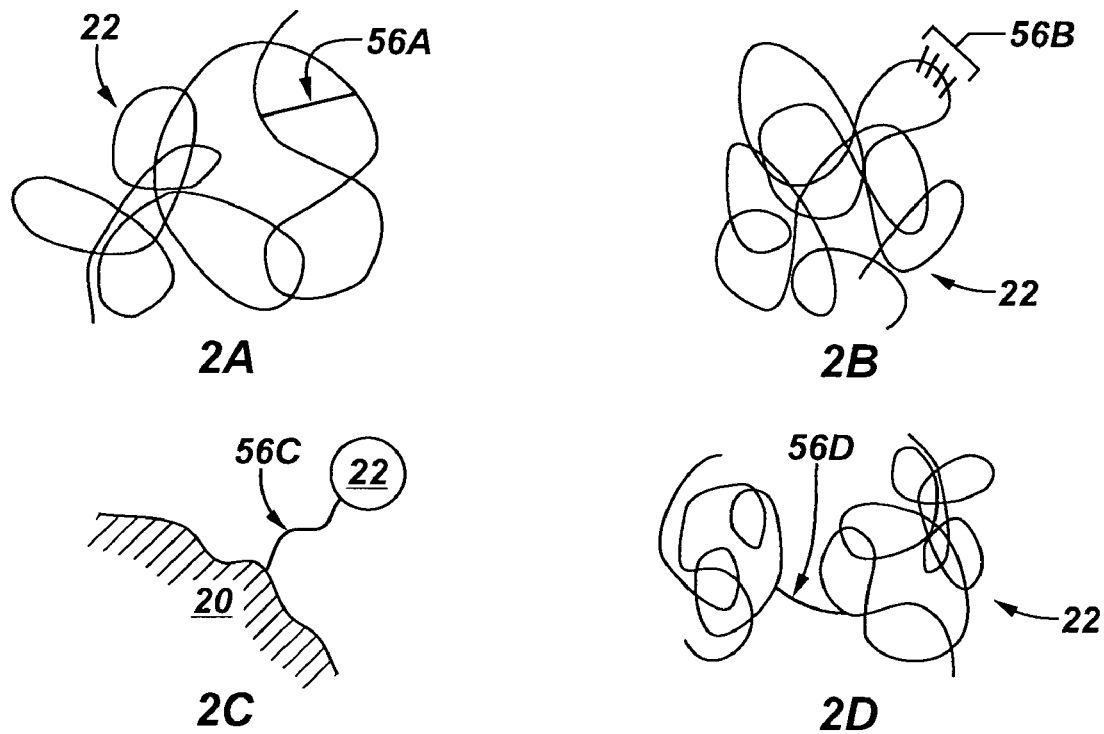
FIGS. 2A, 2B, 2C, and 2D illustrate arrangements of a molecular entity in a fixed relationship to an analyte binding ligand.

With reference to FIG. 2A, molecular moiety 56A may be a linker molecule crosslinking portions of a protein. For example, the molecular entity may be introduced to analyte binding ligand 22 by derivatizing the analyte binding ligand by protein engineering. Thus, the analyte binding ligand 22 may be a protein engineered non-native protein which is stabilized from denaturation at higher temperatures by known methods of protein engineering. For example, analyte binding ligand 22 may be a protein reconstituted from a native form consisting of several monomers to a temperature stable covalently crosslinked multivalent derivative by crosslinking the monomers with a bifunctional linker such as succinimidyl-derivates (e.g. bis[sulfosuccinimidyl]suberate [BS3]). In another embodiment, the analyte binding ligand may also be modified to change physiochemical properties (for example, charge, $pK_a$, hydrophobicity, hydrophilicity) by covalent attachment of chemicals or by chemical conversion of parts of the ligand molecule itself.

With reference to FIG. 2B, molecular moiety 56B may be a non-native peptide in analyte binding ligand 22. For example, analyte binding ligand 22 may be a recombinant protein whose amino acid sequence is modified (exchange of one or several amino acid residues by site-directed mutagenesis) to resist heat-induced degradation and to maintain functionality over a long period of time. The recombinant analyte binding ligand 22 may be generated by random or site-directed mutagenesis, and/or DNA shuffling. For example, one or more mutations may be constructed at a defined or random site(s) in the cDNA of ConA. After these modified cDNA fragments are cloned and expressed in yeast, translated ConA-mutants may be screened for their ability to sustain binding to glucose at elevated temperatures and compared to the wild-type ConA. Temperature stable recombinant ConA is selected. In addition, DNA-shuffling or gene scrambling may also be used to randomly fragment cDNA of ConA by DNAaseI digestion, followed by re-assembling by recombination with each other, and screening and selecting temperature stable clone.

With reference to FIG. 2C, molecular entity 56C may a a chemical linker between analyte binding ligand 22 and macroporous hydrogel matrix 20. For example, another type of analyte binding ligand 22 may be a native, recombinant, or engineered protein that is stabilized by being chemically bound to the surface of the macroporous hydrogel matrix layer and/or throughout macroporous hydrogel matrix 20 by means of a chemical linker. In this embodiment, the molecular moiety is the chemical linker. The chemical linker may contain specific functional groups for effective binding to both the specific sites of macroporous hydrogel matrix 20 and the analyte binding ligand 22. For example, matrices with hydroxyl groups may be pre-activated with epoxy groups using epichlorohydrin, or with vinyl groups using divinylsulphone, under alkaline conditions, followed by immobilization of the protein at pH 9. Analyte binding ligand 22 may be linked to macroporous hydrogel matrix 20 by reactive chemicals capable of forming a covalent bond by external activation with electromagnetic energy (including but not limited to heat, light and/or x-ray). For example, the crosslinking of the bi-functional linker acryloyl-PEG-NHS (which conjugates to a protein via a succinimidyl ester) can be used to immobilize analyte binding ligand 22 to a hydrogel matrix that contains acrylate end groups. In another embodiment, the length of the linker molecule may control the flexibility of the immobilized analyte binding ligand 22. Typical linker lengths vary from 2 to 25 Å. It will be understand that any suitable linker molecule may be used. For example, suitable linker molecules include aryl azides, carbodiimides, hydrazides, imidoesters, isocyanates, makeimides, succinimidyl (NHS)-esters, vinyl sufones, and pyridyl disulfides.

The degree of resistance to temperature-induced degradation may be controlled by the number of attachment points of the chemical linker 56C with the analyte binding ligand 22 to the macroporous hydrogel matrix 20. A higher number of attachment points provide increased resistance of the analyte binding ligand 22 to denaturation at elevated temperature. Multipoint attachment may be achieved by conjugating a high density of crosslinker groups on the surface of a hydrogel matrix or by changing reaction conditions during immobilization (including but not limited to pH and/or buffer strengths), in order to increase the probability of multipoint cross-links of the ligand with the matrix.

With reference to FIG. 2D, molecular entity 56D may be a crosslinker between monomers forming analyte binding ligand 22. For example, analyte binding ligand 22 may be made of molecularly imprinted polymers (MIPs) containing a plurality of binding sites with high specificity and selectivity to the analyte. In a typical/classical MIP synthesis, the target (or template) molecule is first allowed to interact with a functional monomer in a predetermined orientation. The monomer-template interaction can be reversible covalent bonding, non-covalent bonding or metal ion coordination. This monomer-template complex is then copolymerized with a crosslinker, leading to a highly cross-linked macroporous polymer with the imprint molecules in a sterically fixed arrangement. After removal of the template molecules, recognition sites that bind specifically to the target molecules are established.

When the analyte binding ligand 22 is a synthetic analyte binding ligand it may also be composed of nucleic acid polymers, such as deoxyribonucleic acid (DNA) or ribonucleic acid (RNA), forming a synthetic analyte binding ligand and a plurality of ligands with various affinities to the analyte. In this embodiment, the molecular entity is a nucleic acid-based monomer forming analyte binding ligand 22.

Macroporous Hydrogel Matrix

With reference to FIG. 1, macroporous hydrogel matrix 20 may comprise porous agarose beads (e.g. Sepharose™), porous polyacrylamide, Sephacryl™, Superdex™, or other crosslinked hydrogel matrix. The exclusion volume of these materials is larger than the molecular weight of the binding ligand (e.g., for ConA (100,000 Da)) and the macromolecular analyte analogue 50 (e.g., for dextran 70,000 Da) to ensure non-hindered diffusion of analyte analogue into and out of the macroporous hydrogel matrix 20. The diameter and size of the bead-matrix may be optimized to maximize the amount of conjugated binding ligand and dyes, and for response time of the assay. Smaller beads have a larger surface area per volume which provides for an increased amount of immobilized ligand and reporting moieties. Optimal bead sizes range from 1 to 50 microns. Such bead sizes may be accomplished by mechanical means generating disruptive shear-force, such by shredding with a homogenizer, pestle, or with a fast rotating tool. Another means is to control bead size during synthesis, followed by particle size analysis and selection. To ensure short diffusion distances for reversible binding of analogue with immobilized ligand, the packaging density of the macroporous hydrogel matrix 20 inside the housing 14 may be between 50 and 80%. At this level of occupancy, the beads are evenly distributed throughout the sensor housing. Round or oval bead geometry may be preferred, since the diffusion path length for analyte from bead surface to the lumen is equidistal.

Analyte Analogue

With reference to FIG. 1, analyte analogue 50 may be selected so as to be capable of being bound by analyte binding ligand 22. Analyte analogue 50 as part of the analyte sensing device 10 may be a water-soluble polymer with a molecular structure including but not limited to branched, star-like, linear, or random coil. The molecular weight may be within 30 and 200 kDa, but preferentially between 50 and 100 kDa. In one embodiment, analyte analogue 50 may be dextran, a branched polysaccharide consisting of glucose residues, which binds to the analyte binding ligand ConA in the absence of glucose. Analyte analogue 50 may also be a linear or branched dendrimer (Ibey et al., *Anal. Chem.* 77: 7039-7046 (2005)), natural or synthetic polymer with specific sugar residues, or a glycosylated protein (e.g. mannosylated bovine serum albumin). In another embodiment, when analyte analogue 50 is polymeric, analyte analog 50 may be chemically modified with terminal glucose-specific sugar residues, including but not limited to lactose, maltose, 2-deoxyglucose, or mannose. The analyte analogue derivatized with one of the sugars may be capable of changing the glucose-dependent signal sensitivity and detection range of analyte sensing component 12 according to the required glucose concentration in the sample fluid.

Arrangements of First Reporting Moiety and Modulating Moiety

First reporting moiety may be covalently attached to the analyte binding ligand 22 and modulating moiety 25 may be covalently attached to analyte binding ligand 22 and vice versa. Labeling of analyte binding ligand 22 and the analyte analogue 50 with first reporting moiety 24 and modulating moiety 25 is interchangeable without compromising the efficiency of the measured changes of the sensing component, which may remain dependent on the analyte 52 concentration. When analyte binding ligand 22 is labeled with first reporting moiety or modulating moiety 25, it may be advantageous that analyte binding ligand 22 contains or is bound to a molecular moiety, as described above.

Figure 3:
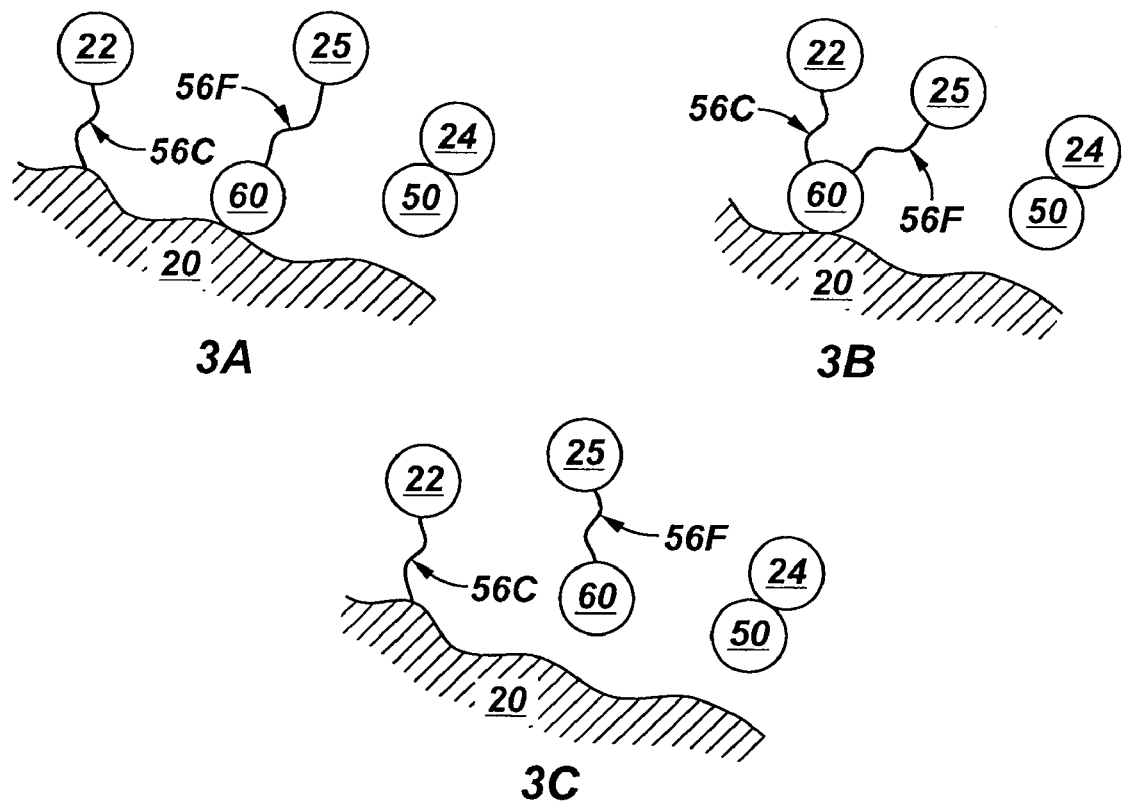
FIGS. 3A, 3B, 3C illustrate arrangements of a molecular moiety in a fixed relationship to a modulating moiety.

Analyte binding ligand 22 may be untagged, that is not attached to first reporting moiety 24 and, in conjunction, not attached to modulating moiety 25. For example, with reference to FIGS. 3A and B and 4A and B, analyte binding ligand 22 may be covalently attached to a macroporous hydrogel matrix 20 in proximity to a carrier entity 60 covalently labeled with the first reporting moiety 24 or modulating moiety 25. [43c] For example, when carrier entity 60 is a protein, such as bovine serum albumin, it be immobilized to a macroporous hydrogel containing epoxy groups first, followed by immobilization of analyte binding ligand 22 with a bifunctional succinimidyl-containing crosslinker such as BS3 or DSS onto the formed layer of dye-labeled carrier entity.

With reference to FIG. 3C, analyte binding ligand 22 may be immobilized to macroporous hydrogel matrix 20 and carrier entity 60 is free of macroporous hydrogel matrix 20. In this embodiment, a molecular entity 56F is the linkage of first reporting entity 24 or modulating moiety 25 to carrier entity 60. Another molecular entity 56C may be a linker molecular disposed between analyte binding ligand 22 and macroporous hydrogel matrix 20.

Figure 4:
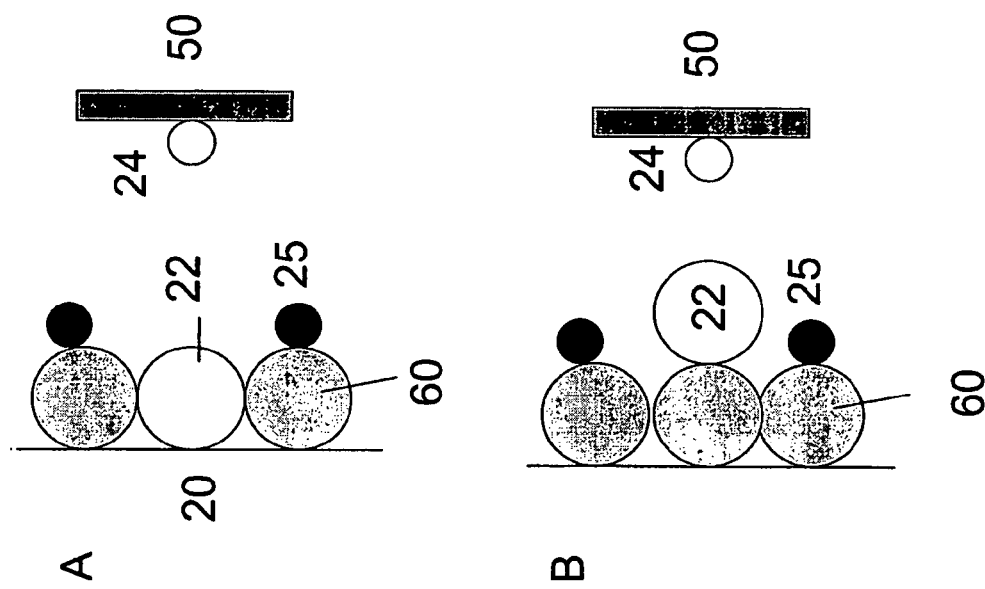
FIGS. 4A and 4B illustrate arrangements of carrier entities carrying a modulating moiety.

As shown in FIG. 4A, analyte binding ligand 22 may be immobilized to a layer of carrier entities 60 immobilized to the macroporous hydrogel matrix 20.

As shown in FIG. 3A and B and 4A and B, the co-crosslinking of analyte binding ligand 22 with carrier entity 60 to the macroporous hydrogel may ensure that the analyte binding ligand 22 will be in close proximity to a dye carried by carrier entity 60. The molar ratio of carrier entity 60 and analyte binding ligand 22 ranges from about 0.2 to about 10, and, in one embodiment ranges from about 2 to about 4, in order to ensure that analyte binding ligand 22 is evenly surrounded by carrier entities 60 when immobilized.

For example, with reference to FIG. 3A, in an embodiment where the analyte 52 is glucose, analyte binding ligand 22 may be Concanavalin A (ConA) and analyte analogue 50 may be dextran, carrier entity 60 may be bovine serum albumin labeled with a non-fluorescent quencher dye QSY21 or ALEXA® 750. ConA and QSY21-BSA may then be immobilized together to a pre-activated macroporous hydrogel matrix 20 containing epoxy groups or cyanogen bromide (CNBr) groups on the surface which are reactive with the amino groups of the BSA and ConA. The molar ratio of QSY21-BSA and ConA is about 1 to about 3. At 100% coverage, the average distance of QSY21 BSA to ConA is typically 50 nm or less.

In each of the embodiments shown in FIG. 3A, 3B, and 3C, analyte binding ligand 22 is stabilized by being unlabelled with any of first reporting moiety 24 and modulating moiety 25. In these embodiments, the molecular moiety 56F is the covalent linkage between dye-carrying entity 60 and a moiety, for example modulating moiety 25. It will be understood that first reporting moiety 24 and modulating moiety 25 is interchangeable without compromising the efficiency of the measured changes of the sensing component, which may remain dependent on the analyte 52 concentration.

Carrier Entity

Carrier entity 60 may be bovine serum albumin. Other suitable choices include water-soluble polymers with functional groups such as other proteins (such as immunoglobulines, lactoglobulin), polysaccharides, glycoproteins, and synthetic polymers.

Mechanism

With reference to FIG. 1, analyte sensing component 12 includes at least one modulating moiety 25. In one embodiment, the conversion efficiency of the first reporting moiety 24 is dependent upon its physical or spatial proximity 59 to modulating moiety 25. First reporting moiety 24 may be chosen such that, when the first reporting moiety 24 is spatially located in close proximity to the modulating moiety 25, a portion of the energy which would be otherwise transmitted and/or released as converted radiation by the first reporting moiety 24 is "leaked" to, "captured" and/or absorbed by modulating moiety 25. In this way, the conversion efficiency of the first reporting moiety 24 is decreased, and the detected radiation of first reporting moiety 24 will be of a lesser amount. Modulating moiety 25 may be a chromophore. The chromophore may be absorbing or fluorescent.

With regard to FIG. 1, in the operation of the analyte sensing device 10 and the analyte sensing component 12, the modulating moiety 25 described above may, in addition to decreasing the efficiency of radiation conversion of the first reporting moiety 24, further decreases the apparent efficiency thereof by absorbing a portion of the provided radiation thus shielding the first reporting moiety 24 from the incident radiation. This secondary effect, which may also be proximity dependent, may result in an even greater change in the detected radiation conversion efficiency of the first reporting moiety upon a corresponding change in analyte concentration. As such, a further enhancement of the sensitivity of the analyte sensing component 12 to the analyte concentration may be realized.

According to an embodiment in which first reporting moiety is bound to analyte analog 50 and modulating moiety 25 is bound to analyte binding ligand 22, since the analyte binding ligand 22 is capable of binding analyte analogue 50 containing first reporting moiety 24 and since modulating moiety 25 is bound to or near to the analyte binding ligand 22, the first reporting moiety 24 may be in close spatial proximity 59 to the modulating moiety 25, and its conversion efficiency concomitantly decreased. As such, in the absence of analyte 52, the number of analyte binding sites available to analyte analogue 50 is increased, and therefore, there is a higher probability that a particular first reporting moiety 24 has its conversion efficiency decreased. In the presence of analyte, certain of the analyte binding sites will be occupied by analyte 52 and, as such, there is a lower probability that analyte analogue 50 will be bound to analyte binding ligand 22. It follows that the probability that a particular first reporting moiety 24 will be in close proximity to the modulating moiety will decrease. Therefore, the apparent average conversion efficiency of first reporting moiety 24 will increase in the presence of the analyte under investigation.

Figure 5:
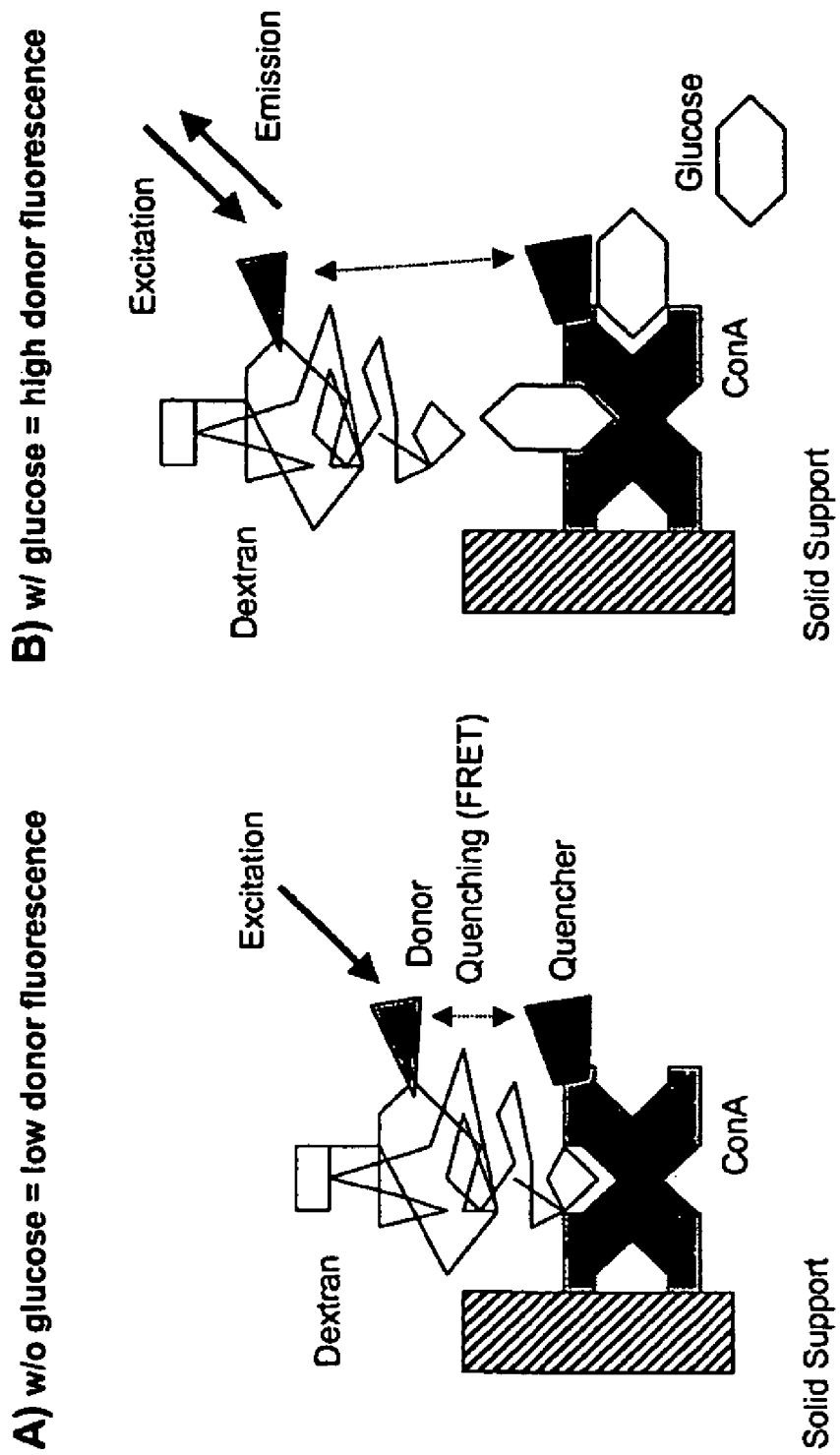
FIGS. 5A and 5B depict embodiments of a FRET-based reaction mechanism of a fluorescence sensor.

When the first reporting moiety 24 is fluorescent, the mechanism by which modulating moiety influences the spectral response of first reporting moiety 24 may be FRET-based. FIG. 5 schematically describes the FRET-mechanism for fluorescence signal generation in the assay. The absorption spectrum of first reporting moiety 24 overlaps with the fluorescence emission spectrum of modulating moiety 25. When the first reporting moiety 24 bound to the analyte analogue 50 is in proximity 59 to the modulating moiety 26 attached to the analyte binding ligand 22 (e.g. concanavalin A, denoted ConA), the fluorescence of the first reporting moiety 24 decreases due to FRET. Upon diffusion of fluorescent analyte analogue 50 (e.g. dextran) away from analyte binding ligand 22 laden support 20 after competitive displacement by analyte (glucose) 52, an increase in fluorescence of the donor dye is observed. The beads act as a solid support 20. This increase is due to an increase in the proximity distance 59 between the donor and quencher dye. At increasing glucose concentrations, the fraction of unbound dextran increases, resulting in the corresponding increase of fluorescence (FIG. 5B). While analyte analog 50 is illustrated as dextran in FIG. 5 and analyte binding ligand is illustrated as concanavalin A in FIG. 5, it will be understood that the above description is not limited to dextran and concanavalin A. When analyte sensing component 12 is FRET-based, it may include any suitable analyte binding ligand and analyte analogue With reference to FIGS. 3A and B and 4A and B, the binding of the analyte analogue labeled with a first reporting moiety 24 or modulating moiety 25 may cause a significant change in fluorescence of the first reporting moiety 24 by the modulating moiety 25 due to their proximity 59. A close proximity arrangement between analyte binding ligand 22 and dye-carrying entity may significantly improve the overall functional response stability of the device at higher temperatures. When dye-carrying entity is bound to matrix 20, and first reporting moiety 24 is fluorescent, the mechanism of modulating moiety influence the spectral response of first reporting moiety 24 may be FRET-based.

With reference to FIG. 3C, as described above, dye-carrying entity 60 and/or a fluorescent nanoparticle (e.g. quantum dot) as first reporting moiety 24 are free from matrix 20. In this embodiment, when first reporting moiety 24 is fluorescent, modulating moiety 25 influences the fluorescence through a non-FRET mechanism in which the modulating moiety changes the transparency of the analyte sensing component to the fluorescence of the first reporting moiety.

First Reporting Moiety

First reporting moiety 24 may be a fluorescent moiety. For example, first reporting moiety 24 may be a fluorescent moiety which exhibits efficient fluorescence quenching capability within the emission wavelength range from about 600 nm to about 800 nm, for example from about 660 nm to about 760 nm. Any radiation absorbing chromophore suitable for efficient absorption within this wavelength range is within the scope of the present invention.

First reporting moiety 24 may emit, generate, modify and/or convert the radiation of the transmitted wavelength(s) to a radiation spectrum that is particularly well transmitted by skin, other body tissues and/or fluids. The spectral region composed of very near-infrared optical radiation is one such portion of the radiation spectrum. Radiation having a wavelength between about 600 nm and about 800 nm is exemplary of near-infrared optical radiation.

When first reporting moiety 24 is a fluorescent moiety, first reporting moiety 24 may be an fluorescent dye, for example an organic fluorescent dye. First reporting moiety 24 may be, for example, Cy7, ALEXA® 750, or ALEXA® 700, ALEXA® 647 (Molecular Probes, Inc.), ALEXA® 680 (Molecular Probes, Inc.), ALEXA® 690 (Molecular Probes, Inc., and/or LD800 (Exciton, Inc.).

Alternatively, when first reporting moiety 24 is a fluorescent moiety, the first reporting moiety 24 may be a fluorescent particle. The fluorescent particle may be organic or inorganic. Further, the fluorescent particle may be metallic or dielectric. Yet further, the fluorescent particle may be conducting or nonconducting. For example, the first reporting moiety 24 may be any one of a TransFluoSphere (Molecular Probes, Inc.), quantum dots, carbon nano tubes, and the like.

Modulating Moiety

Modulating moiety 25 is capable of absorbing at least a portion of provided radiation (from first reporting moiety 24) at one or more wavelengths. Thus, in selecting or choosing a first reporting moiety 24, a corresponding modulating moiety 25 may also be selected which is capable of altering the conversion efficiency of the first reporting moiety 24. Further, modulating moiety 25 that may emit, generate, modify and/or convert the radiation of the transmitted wavelength(s) to a radiation spectrum that is particularly well transmitted by skin, other body tissues and/or fluids.

Modulating moiety 25 may be a fluorescent moiety or a non-fluorescent moeity. Further, modulating moiety 25 may be an organic dye or a metallic nanoparticle, either of which may be fluorescent or non-fluorescent (TRUE? yes). Thus, in one pair, first reporting moiety 24 may be one a fluorescent organic dye and modulating moiety 25 another organic fluorescent dye. In another pair, first reporting moiety 25 may be an organic fluorescent dye, with modulating moiety 25 being a nonfluorescent dye. In yet another pair, first reporting moiety 24 may be an organic fluorescent dye, and modulating moiety 25 a metallic nanoparticle. In still yet another pair, first reporting moiety 24 may be fluorescent particle whereas the modulating moiety 25 may be a fluorescent organic dye or a non-fluorescent dye. It is contemplated, however, that any suitable pair of first reporting moiety 24 and modulating moiety 25 may be utilized.

When modulating moiety 25 is an organic fluorescent dye, modulating moiety 25 may be, for example, Cy7, ALEXA® 750, or ALEXA® 700, ALEXA® 647 (Molecular Probes, Inc.), ALEXA® 680 (Molecular Probes, Inc.), ALEXA® 690 (Molecular Probes, Inc.) and/or LD800 (Exciton, Inc.).

When first reporting moiety 24 and modulating moiety 25 are both organic fluorescent dyes, first reporting moiety 24/modulating moiety 25 pairs may be, for example: ALEXA® 647/Cy7, ALEXA® 647/ALEXA® 680, ALEXA® 680/allophycocyanin (APC), ALEXA® 700/APC, and/or ALEXA® 750/APC, ALEXA® 647/ALEXA® 700, ALEXA® 647/Cy7, ALEXA® 647/ALEXA® 680 (Molecular Probes, Inc.). It is contemplated, however, that any suitable pair of organic fluorescent and/or non-fluorescent dyes may be utilized.

When nodulating moiety 25 is a non-fluorescent dye, modulating moiety 25 may be for rexample QSY21. When first reporting moiety 24 is a fluorescent dye and modulating moiety 25 is a non-fluorescent dye, first reporting moiety 24/modulating moiety 25 pairs may be, for example: dye pairs: ALEXA® 647 /QSY21, Cy5/QSY21.

When modulating moiety 25 is a metallic nanoparticle, the metallic nanoparticle may include gold and/or silver. Further, when modulating moiety 25 is a metallic nanoparticle, modulating moiety may be covalently attached to another entity, such as macroporous hydrogel matrix 20, analyte binding ligand 22 or analyte analog 50, and/or dye-carrying entity 60. For example, when the metallic nanopartice is a gold nanoparticle, it may be covalently attached with thiol-specific crosslinkers via functional thiol groups on the surface of the gold nanoparticle. When first reporting moiety 24 is a fluorescent organic dye and modulating moiety 25 is a metallic nanoparticle, the metallic nanoparticle may reduce or enhance the fluorescence emission of the fluorescent organic dye, which represents the first reporting moiety in this case, as was shown for certain gold-nanoparticles in close proximity with fluorescent dyes (Lakowicz et al. *J Fluoresc* 2002, 12, 299-302.)

When first reporting moiety 24 is a fluorescent organic dye and modulating moiety 25 is a metallic nanoparticle, a metallic nanoparticle may be used in combination with any suitable organic fluorescent dye, such as any one of those disclosed herein.

When first reporting moiety 24 is a fluorescent organic dye and modulating moiety 25 is a fluorescent nanoparticle, the fluorescent nanoparticle may reduce or enhance the fluorescence emission of the fluorescent organic dye.

Second Reporting Moiety

With reference to FIG. 1, a second reporting moiety 26 may be selected and/or designed to include a conversion efficiency which is independent (or substantially independent) of the concentration of analyte under investigation. In this way, the change in conversion efficiency which is dependent on the concentration of analyte 52 may be more readily deduced by comparing the amount of detected radiation of the first wavelength(s) and the amount of detected radiation of the second wavelength(s). The normalization of the fluorescence of the first reporting moiety 24 provides an analyte-concentration specific output which is independent of unspecific effects due to changes in the absorptive or fluorescent properties of the solution or matrix surrounding the analyte sensing device 10, due to changes of the output of the radiation providing unit 28, or due to photobleaching of the fluorescent dyes employed.

Figure 6:
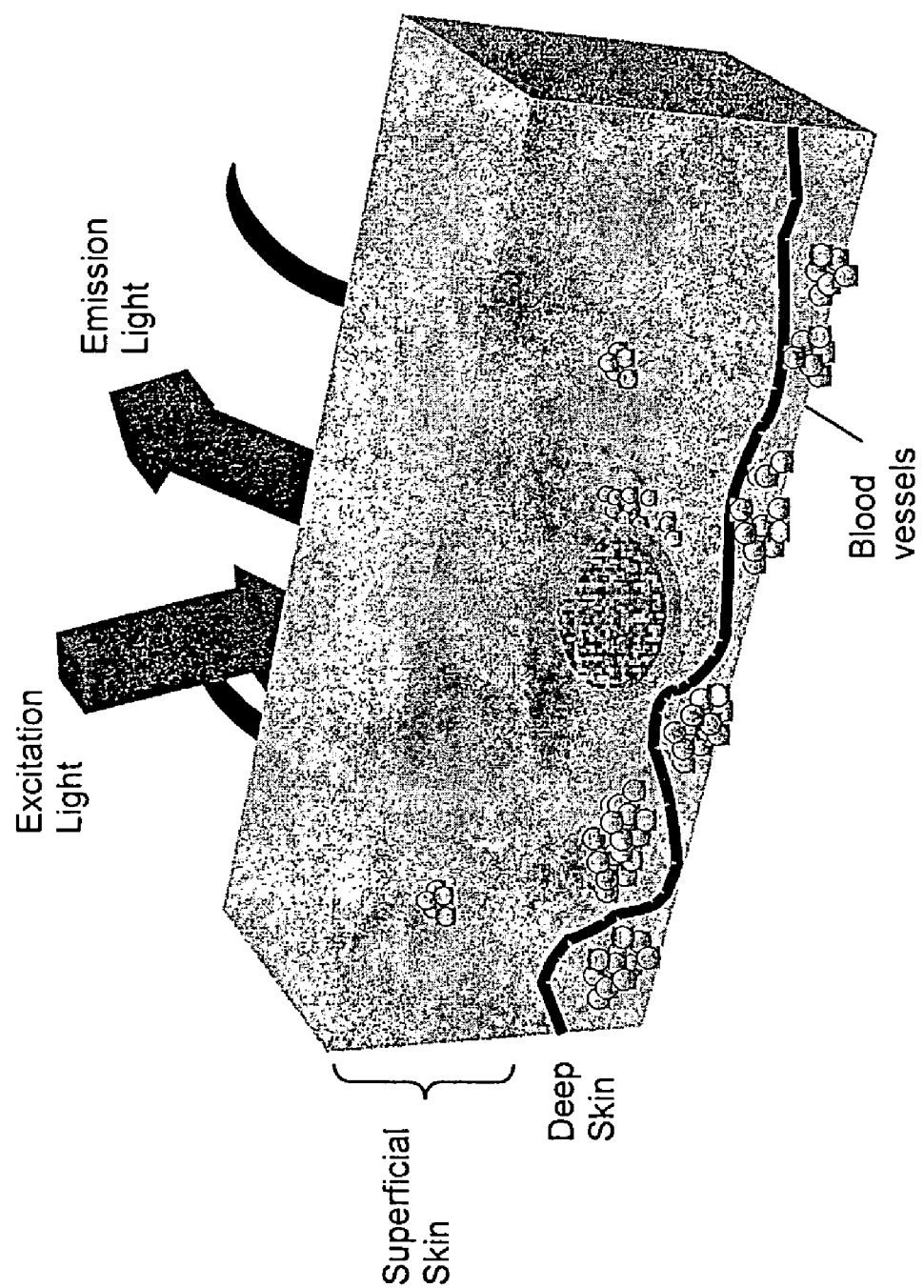
FIG. 6 illustrates one type of implanted analyte sensing device.

With reference to FIG. 6, attenuation or alteration of the transmission of both provided radiation 34 and detected radiation 36 may be caused by skin, body tissues and/or fluids, as well as previously described factors. As such, the first and second reporting moieties 24 and 26 may be chosen so that these effects are the same or substantially the same for the wavelength(s) of the converted or modified radiation. Thus, where the analyte sensing device 10 includes first and second reporting moieties 24 and 26, the difference in detected amounts of the analyte-sensitive first converted radiation and the analyte-insensitive second converted radiation may be related to the concentration of analyte 52 surrounding the analyte sensing components 12.

With reference to FIG. 1, the second reporting moiety 26 may be a fluorescent organic dye or fluorescent nanoparticle, capable of converting optical radiation between 630 and 650 nm into optical radiation between 650 and 850 nm. The second reporting moiety 26 may be included as a polymer-crosslinked dye, or incorporated into macroporous beads by physiosorption or covalent chemical attachment. In one embodiment, the second reporting moiety 26 is embedded inside nanospheres made of polystyrene, polycarbonate, or PMMA, forming nanoparticles. The surface of such nanoparticles may be coated with chemicals by physiosorption or by covalent chemical attachment that prevent nanospheres from adhering to each other. For example, a silica surface may be pre-activated with derivatives of aminopropylsilane (APS) and reacted with a bifunctional crosslinker such as glutaraldehyde, or a succinimidyl derivative (DSS) for crosslinking with BSA or aminodextran. The diameter of such nanoparticles is large enough to prevent their access into the macroporous hydrogel matrix, where it can block receptor sites for dextran binding, but small enough to prevent settlement by gravity. Bead sizes ranging from 150 to 250 nm may be preferred.

With regard to FIG. 1, the technique of providing radiation to the analyte sensing device 10 may also be modified to better facilitate the detection of the change in the conversion efficiency of the first and second reporting moiety(s) 24, 56 of the analyte sensing component 12. For example, the provided radiation may be temporally modulated in intensity and/or wavelength, and the temporal intensity and/or wavelength of the detected converted radiation may be used to determine the radiation conversion efficiency of the reporting moieties of analyte sensing component 12. The provided radiation may be temporally modulated in intensity according to a periodic sinusoidal profile. The detected converted radiation will also then exhibit a temporal sinusoidal intensity variation. The phase of the sinusoidal intensity variation of the detected converted radiation relative to the provided radiation may be used to determine the conversion efficiency of the reporting moieties and hence relate to the analyte concentration.

It will be understood that when an analyte sensing component includes a second reporting moiety, the second reporting moiety may be identical with the modulating moiety (not shown). Thus, a common moiety may act as a modulating moiety and a second reporting moiety. That is, a common moiety may modulate the spectral response of the first reporting moiety and also have a spectral response independent of the concentration of glucose. Thus, a modulating moiety may act as a second reporting moiety. That is, a modulating moiety may have a spectral response that is independent of the concentration of glucose. The concentration of glucose may be the concentration of glucose in the housing.

Housing

With reference to FIG. 1, housing 14 may be partially constructed of an impermeable material, and may be constructed in whole or in part of a selectively permeable material. A selectively permeable material allows for continual equilibration between the external analyte concentration and the internal analyte concentration by allowing the analyte to cross a semipermeable membrane 18. A semipermeable membrane 18 constrains analyte sensing components 12 so that the components may not leave the interior formed by the housing 14.

With regard to FIG. 1, the sensor housing 14 may comprise an impenetrable portion 16 and a perforated, semipermeable portion for analyte diffusion in and out of the sensor housing 14. The materials of the impenetrable and penetrable portion may be chosen according to the requirements of the particular application. The sensor housing 14 should exhibit a low tendency for host rejection. Materials of choice for the impenetrable portion include but are not limited to polyurethane, polysulfone, silicone or titanium. Materials of choice for the semipermeable portion of the housing include but are not limited to regenerated cellulose derivatives, PEG, porous polyurethane, or perforated silica. The thickness of the analyte-permeable portion 18 should be less than 200 microns, preferably 20 to 30 microns to allow fast diffusion of the analyte (e.g. glucose). The size of the sensor housing is preferably small (large membrane area/volume ratio), in order to minimize the time the analyte needs for diffusion to the point farthest from the semipermeable portion inside the lumen of the housing. In one embodiment, the sensor housing comprises one or several short segments of hollow fiber membranes (e.g. made of regenerated cellulose) having an overall diameter of approximately 220 microns and a membrane thickness of 20 microns. The diffusion distance for glucose from the outside of the semipermeable portion of the housing to the lumen of the housing is approximately 100 microns. Other housing geometries with similar diffusion lengths are preferred.

With reference to FIG. 1, where the semipermeable portion (membrane) needs to be sealed to the housing with adhesive, the membrane may be chemically pre-treated with chemical groups to enhance chemical compatibility, resulting in improved physical integrity. For example, when using epoxy-based adhesives, cellulose-based membranes may be covalently conjugated with epichlorohydrin to introduce epoxy groups onto the surface of the membrane, or when using cyanoacrylate-based adhesives, the attachment of amino- or hydroxyl groups may be preferred.

Figure 7:
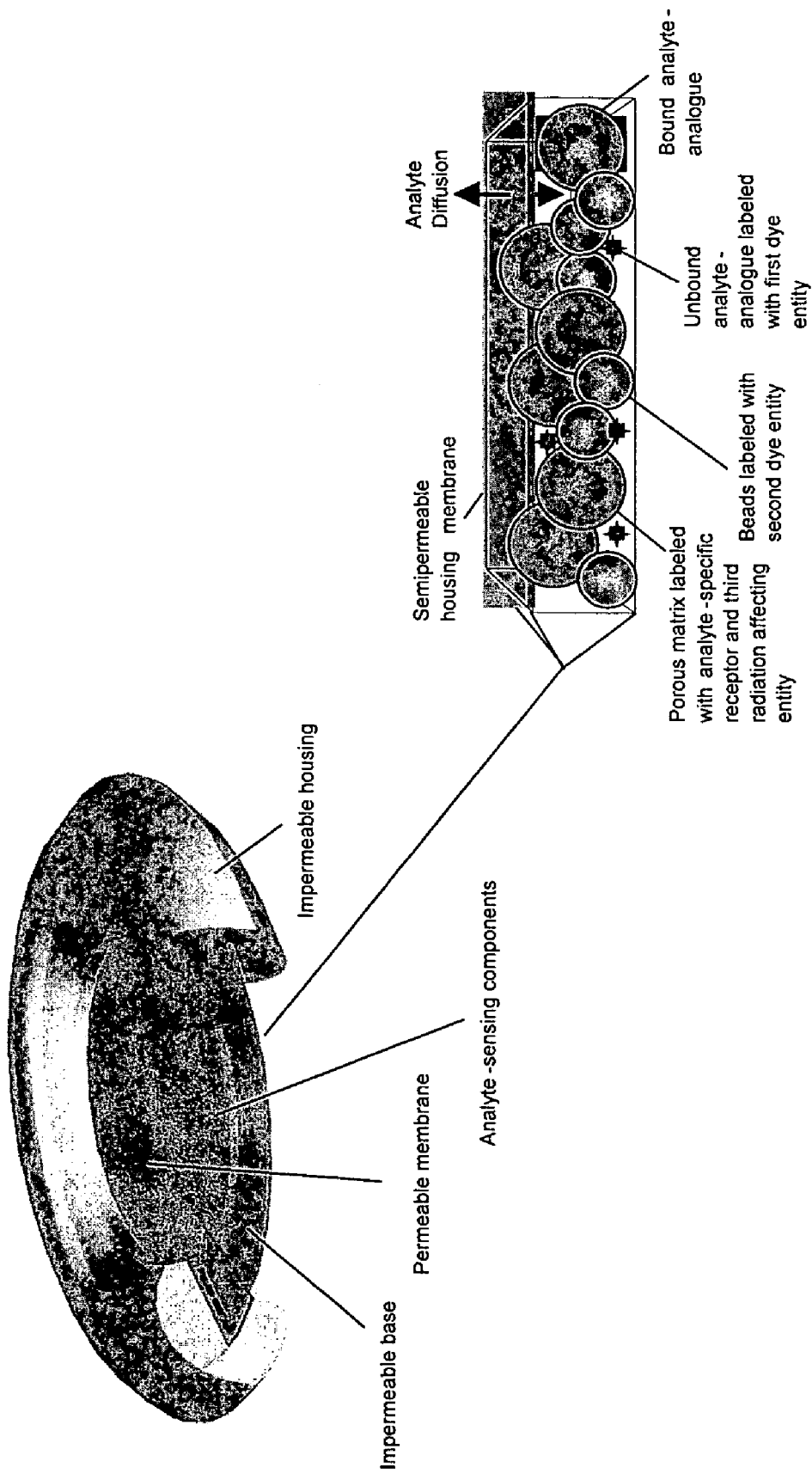
FIG. 7 illustrates an analyte sensing portion of an analyte sensing device.

With reference to FIG. 7, in an effort to enhance communication of the analyte sensing device 10 with the surrounding environment, the permeability or surface area of membrane 18 may be increased. This may be accomplished by increasing the length/width of membrane and, as such, the size of the analyte sensing device. In addition, the analyte sensing device of FIG. 7 may include a membrane on both "sides" of the analyte sensing device. Membranes 18 may "sandwich" the analyte sensing component. In this way, fluid communication with the surrounding environment is increased and the communication of analyte into and out of the analyte sensing device is enhanced. It will be understood that the disclosure herein with reference to FIG. 7 is not limited to the particular arrangement of moieties (e.g. first reporting moiety, modulating moiety, and second reporting moiety) shown in FIG. 7, but may apply to any arrangement of moieties disclosed herein, such as with reference to FIGS. 3 and 4, and further when modulating moiety 25 and second reporting moiety 26 are either distinct (as shown in FIG. 7) or identical (not shown).

Figure 8:
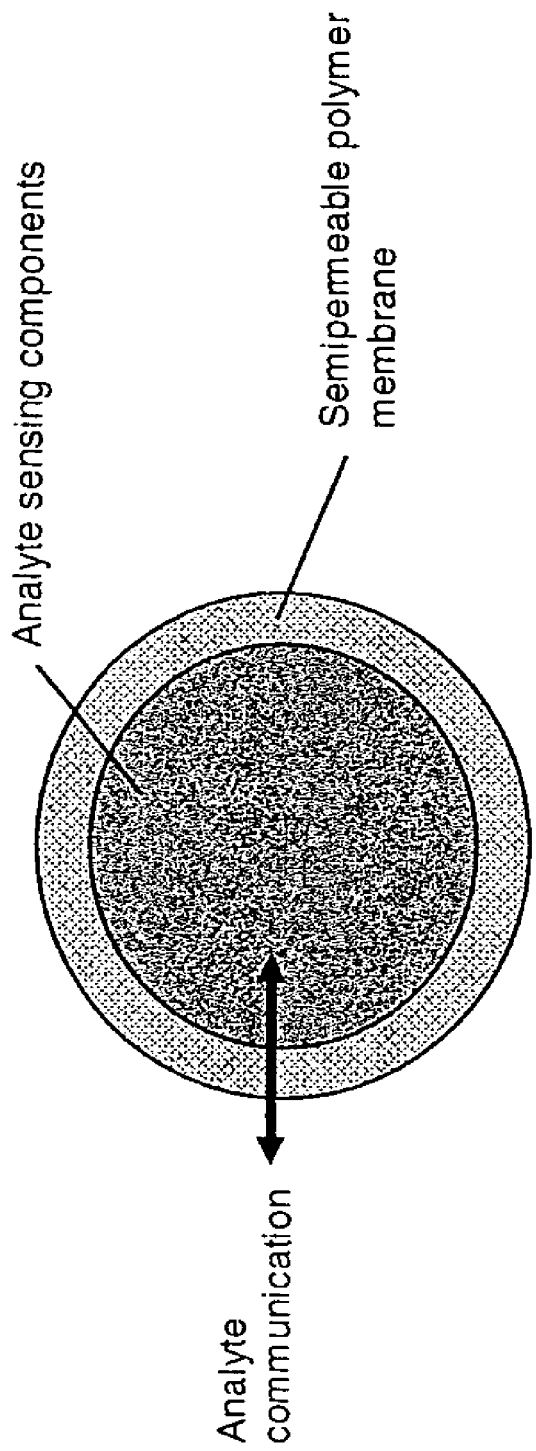
FIG. 8 schematically depicts a polymer encapsulated analyte sensing device.

With regard to embodiments shown in FIG. 8, for rapid sensing of analyte concentration, it is desirable that the communication of analyte into and out of the analyte sensing device 10 be as rapid as possible. The rate of analyte concentration can be enhanced by increasing the permeability of the semi-permeable portion of housing (the membrane). The rate of communication may also be enhanced by increasing the surface area of membrane relative to the fluid under investigation. In those instances where the housing 14 is comprised of a polymer, the surface-area-to-volume ratio of the analyte sensing device 10 may be at least partially impact the rate at which the analyte binding ligand 22 may respond to a change in analyte 52 concentration in the fluid under investigation. It may therefore be desirable, for example, to include or employ a plurality of analyte sensing devices 10 and/or components having a small spherical shape rather than a single spheroid of similar total volume.

Figure 9:
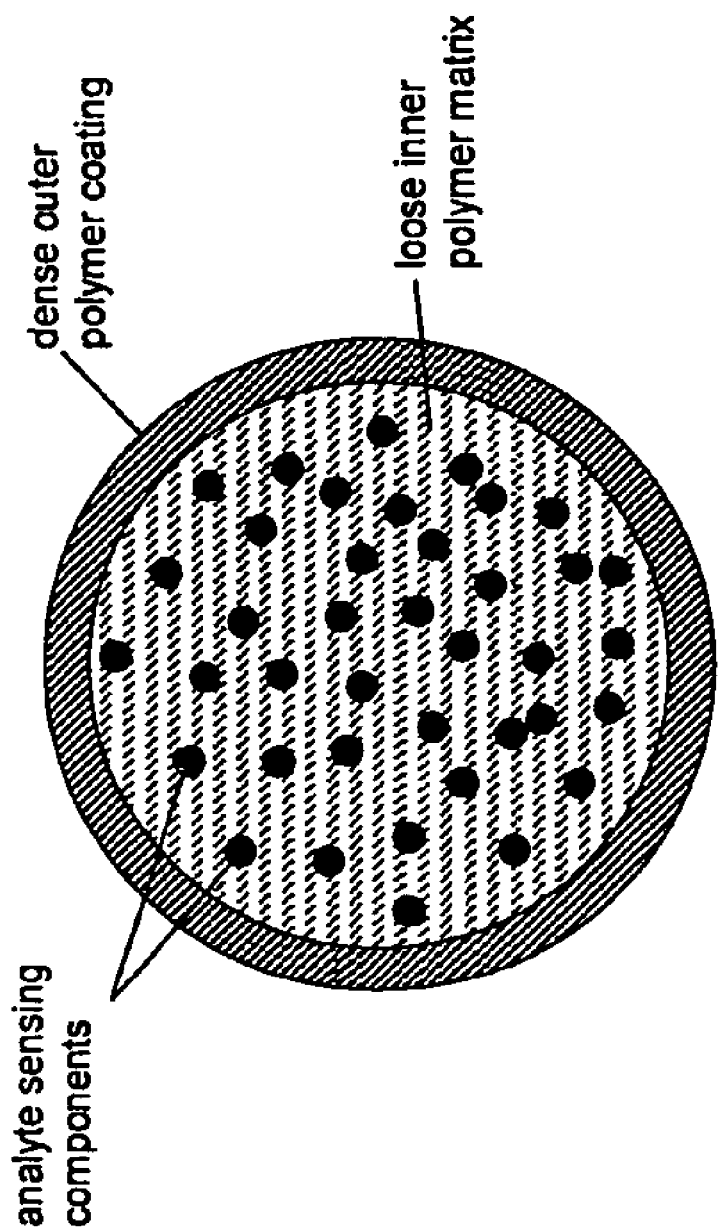
FIG. 9 illustrates another type of polymer encapsulated analyte sensing device.

With reference to FIG. 9, the analyte sensing component 12 may be contained within the polymeric matrix. In such an embodiment, the housing 14 may comprise a polymer 42 (hereinafter referred to as polymeric housing) and a permeable capsule 18 or semi-permeable capsule which contains, maintains and/or retains the analyte sensing chemistry (i.e., the analyte sensing components 12) while allowing the analyte concentration within the surrounding fluid to vary by movement of analyte 52 into and out of the semi-permeable capsule. The polymeric housing may selectively or entirely surround the polymeric matrix containing the analyte sensing components 12. Alternatively, the analyte sensing component 12 may be embedded throughout the polymeric matrix formed by or comprised of the material of the polymeric housing.

With reference to FIG. 8, it may be advantageous to employ a polymeric housing that is permeable to the analyte of interest and that permits movement of the ligands 22 and analyte analogues 50 within the interior of the capsule without permitting "escape" from the housing 14. For example, the polymeric housing may be comprised of polyethylenegycol (PEG) and/or synthetic derivatives thereof, calcium phosphate, polyurethane, alginate, regenerated cellulose acetate, chitosan, or combinations thereof It may be advantageous to employ polymers having cross-linking density, porosity and/ or swelling properties that may be adjusted to meet the environmental requirements of the analyte sensing device 10. Techniques for adjusting such properties are well known to those skilled in the art.

With reference to FIG. 9, the housing 14 may be constructed from one or more discrete polymeric formulations to provide the desired properties. For example, the analyte sensing device 10 may be constructed of a polymeric matrix containing analyte sensing components 12 and forming a core around which a second more dense polymeric capsule is formed.

In Situ Formation

With reference to FIG. 9, the analyte sensing device 10 may be formed in situ. A liquid precursor may be injected into or under the skin surface and thereafter a polymeric housing 14 is formed around the liquid precursor. The liquid precursor may include, for example, a macroporous hydrogel matrix layer 20, an analyte binding ligand 22, a first reporting moiety 24, modulating moiety 26 and modulating moiety 54. The analyte sensing device of this embodiment may be formed using transdermal (through the skin surface) photo initiated cross-linking polymerization. The liquid precursor may comprise analyte binding ligands 22 mixed or co-dissolved with a polymer precursor solution. The analyte binding ligands 22 may be free in the solution, or may already be covalently tethered to a portion of the monomer in the precursor mixture.

With regard to FIG. 9, the polymer precursor solution may contain unlinked monomers and a photoinitiator to initiate cross-linking of the monomers subsequent to activation by suitable optical radiation. For example, a PEG-diacrylate or PEG-dimethacrylate monomer may be dissolved in water and co-dissolved with a photoinitiator such as dimethoxyphenyl acetophenone (DMPA) or hydroxyphenyl ketone (HPK). Upon irradiation with light at approximately 365 nm, the photoinitiator forms a free radical which attacks carbon-carbon double bonds in acrylated or methacrylated termini of PEG monomer chains. These attacked sites in turn attack other PEG termini, thereby forming stable cross-linked networks of PEG polymer. In this way, photoactivation is used to initiate polymerization of the sensor housing component.

With regard to FIG. 9, it should be noted that a sufficient amount/intensity of radiation having a wavelength in the range of 365 nm may be delivered through skin such that a precursor mixture injected in liquid form may be made to polymerize by providing polymerization initiating radiation from outside the animal body.

With reference to FIG. 9, yet another technique for polymerizing analyte sensing device 10 subsequent to injection of the precursor mixture is to utilize a temperature sensitive polymer formulation 42. Several polymers are well known to those skilled in the art to have very sharp phase transitions over narrow temperature ranges. A polymer which is a solid or gel at body temperature but is a liquid at slightly higher temperatures could be warmed to a liquid and injected into or below the skin. As the precursor cools, it gels into an analyte sensing device 10. Other techniques of controlling the phase of the polymer may be utilized. Other techniques include but are not limited to controlling the phase of the polymer via pH dependence.

With reference to FIG. 9, while illustrated as substantially spherical, analyte sensing device(s) and/or component(s) may be of any shape. Similarly, in the creation of a polymer from a liquid precursor mixture, it may be desirable to construct the analyte sensing device 10 with a large surface area relative to its total volume. One way for realizing such a configuration can be accomplished by adding an additional forming component to the precursor mixture. In one embodiment, the forming component may be injected with the precursor mixture and act to increase the surface area of the polymerized sensor. For example, the forming component may be oil or other liquid which is immiscible in/with the polymer/sensor precursor mixture. By shaking or otherwise agitating the resulting mixture, the phases may form in part or in total an emulsion consisting of small local domains of sensor precursor interspersed with small local domains of the forming component. The resulting emulsion may take on a "frothy" appearance. Injection and subsequent polymerization of such an emulsion can be made to result in a polymer with a large number of voids and "bubbles" 48 resulting from the presence of the forming component. If the forming component is inert and eventually leeches away or is otherwise removed from the resulting polymer sensor structure, a sensor with a highly porous macrostructure and hence highly contorted surface will result.

Analyte Sensing System

With reference to FIG. 1, a system according to one embodiment of the present invention includes an analyte sensing device 10, radiation providing unit 28, radiation detecting unit 30 and signal analyzer and output unit 32. The radiation providing unit 28 provides transmitted radiation 34 (e.g., optical radiation having a first wavelength or wavelengths) to the analyte sensing device 10. In response to transmitted radiation 34, which is incident thereon, the analyte sensing device 10 converts at least a portion of the radiation of the first wavelength(s) to radiation having different wavelength(s). In this regard, transmitted radiation impinges upon analyte sensing components (having the analyte sensing chemistry) and at least a portion of the radiation is converted to radiation of a different wavelength(s). The radiation detecting unit 30 measures, senses, detects and/or samples radiation. The signal analyzer and output unit 32 uses that data to determine, calculate, assess and/or detect the concentration of analyte 52 in the fluid under investigation and outputs data (analog or digital) which is representative thereof.

With reference to FIG. 1, the radiation providing unit 28 may include, for example, a laser operating at a wavelength between 630-650 nm. As such, the transmitted radiation 34 includes energy having a wavelength between 630-650 nm. In one embodiment the laser provides optical radiation having a wavelength of 645 nm.

With reference to FIG. 1, in another embodiment, the incident energy having a wavelength between 630-650 nm may be converted and/or modified to an optical radiation having a wavelength of approximately 675 nm. In this regard, a portion of transmitted radiation 34 is converted and/or modified by the first reporting moiety 24 that is, for example, unbound or bound to analyte binding ligand 22. At least a portion of the converted and/or modified transmitted radiation (i.e., modified radiation), is transmitted through the housing and received, sensed, sampled, detected and/or measured by radiation detecting unit 30.

With reference to FIG. 1, in one embodiment the housing 14 may contain a plurality of second reporting moiety 26, in addition to optical radiation having a wavelength of approximately 675 nm, may also include a component that includes a wavelength of approximately 725 nm. The radiation of the second wavelength may be generated by the second reporting moiety 26 which is transmitted through the housing 14. In this embodiment, the radiation detecting unit 30 senses, samples, detects and/or measures at least a portion of the modified or converted radiation that is transmitted through housing 14.

With reference to FIG. 1, the radiation detecting unit 30 may include optics and electronics to sense, sample, detect and/or measure radiation having one or more wavelengths. For example, in the embodiment including a modulating moiety 25 (i.e., organic dyes, beads or particles), the radiation detecting unit 30 may sense, sample, detect and/or measure modified or converted radiation which includes energy having at least two wavelengths.

With reference to FIG. 1, the radiation detecting unit 30 may include a plurality of radiation detecting devices, each device being capable of sensing, sampling, detecting and/or measuring a wavelength-specific portion of the modified or converted radiation (e.g., the wavelength of the radiation generated, converted and/or modified by the first reporting moiety).

With reference to FIG. 1, the radiation detecting unit 30 may include one or more photodiode detectors and wavelength specific optical filters. The radiation detecting unit 30 may also be, for example, a charge-coupled device (CCD) array and a dispersive unit (i.e. a spectrograph). The radiation detecting unit 30 may also be combinations or permutations thereof, or may include other instrumentation for detecting converted or modified radiation.

With reference to FIG. 1, the amount of converted radiation sensed, sampled, detected and/or measured by the radiation detecting unit 30 may depend upon, for example: (i) the amount of transmitted radiation which is incident on and/or reaches the first or second reporting moieties 24, 26 (which in turn depends on the intensity of the transmitted radiation provided by the radiation providing unit), (ii) the efficiency of the "delivery" to the device and the transmissivity of housing; (iii) the conversion efficiency of the first and second reporting moieties; and (iv) the efficiency with which the converted radiation is transmitted back to the radiation detecting unit (which depends in part on the transmissivity of the housing to the converted radiation, the efficiency of the transmission of converted radiation to the radiation detecting unit, and the physical arrangement of radiation detecting unit 30 with respect to the analyte sensing device 10. In an embodiment employing at least two reporting moieties, the first and second reporting moieties 24 and 26 are chosen so that all elements of (i) through (iv) are the same or substantially the same for each wavelength of converted radiation. In this way, differences in the relative amounts of detected radiation of the first and second wavelengths by radiation detecting unit 30 depend, to a significant extent, on the conversion efficiency of each reporting moiety.

With regard to FIG. 1, the radiation providing unit 28 and/or the radiation detecting unit 30 may also be integrated into the housing 14 of the analyte sensing device 10 to provide a more self-contained device.

Implanted Sensor

With reference to FIG. 7 *a* and *b* the analyte sensing device 10 without optical fibers (FIG. 7A) and with optical fibers 88 (FIG. 7B) may be implanted under the skin 40 into the dermis tissues of the body of an animal. Such implantation may be accomplished by making a small incision in the skin surface and tissue into which the analyte sensing device may be inserted, implanted, disposed, placed and/or affixed. Any technique for inserting, implanting, disposing, placing and/or affixing analyte sensing device(s) into the animal body may be utilized.

Figure 10:
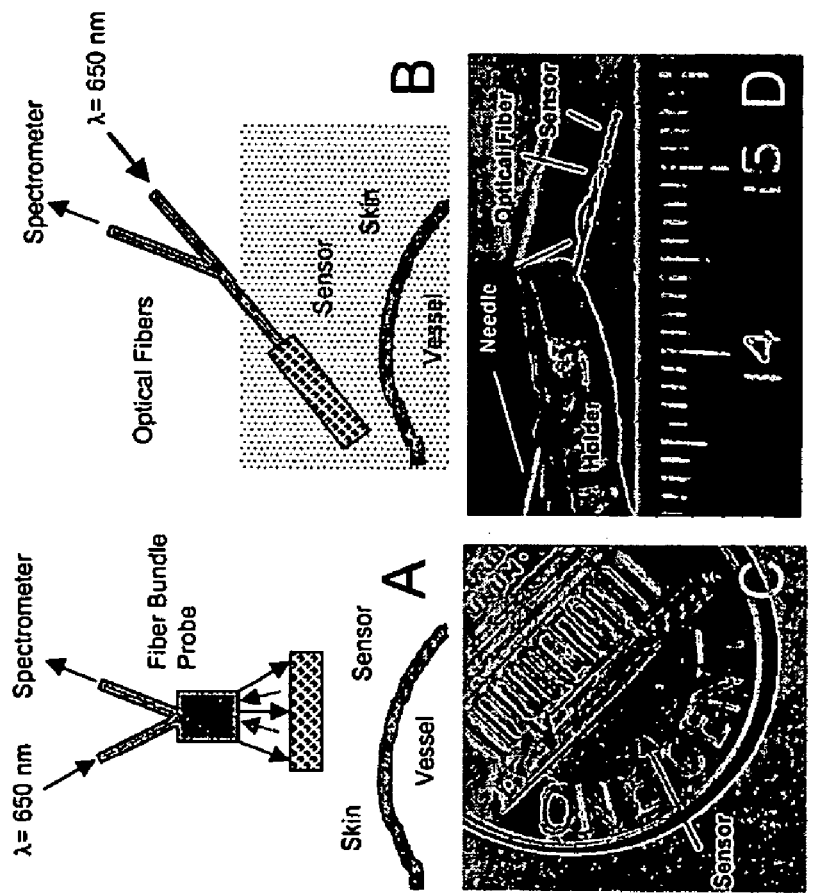
FIG. 10 illustrates two techniques for interrogating an analyte sensing device.

With reference to FIG. 10B, the radiation providing unit 28 and/or the radiation detecting unit 30 may be physically connected with the analyte-sensing device 10 via radiation transmitting optical fiber(s) 88. To facilitate detection and measuring, the housing of device 10 containing the analyte sensing components 12 may be physically connected to the distal end of the optical fiber 88. The converted radiation may be transmitted back through the optical fiber 88 to the radiation detecting unit 30 where it is measured.

With reference to FIG. 10B, in order to improve chemical compatibility between the semipermeable portion of the housing of device 10 (e.g. hollow fiber membrane made of regenerated cellulose) and the optical fiber 88, both components maybe pre-functionalized with specific groups. For example, when using cyanoacrylate as adhesive, aminogroups may be attached to the surface of the optical fiber 88 and the housing of device 10 by covalent chemistry. Also, optical fibers 88 made of glass may be pre-treated with aminosilan derivatives (e.g. aminopropyl-triethoxysilan) to covalently attach terminal aminogroups onto the glass surface. Covalent attachment of amino-dextran or ethylendiamine onto the hollow fiber membrane housing may also be facilitated through various crosslinker molecules (e.g. DVS (divinyl sulfone)).

With regard to FIG. 10A and B, when the analyte-sensing device 10 is placed in skin tissue, the properties of the outer surface of the housing that interface with tissue may be modified with a biocompatible coating of molecules to prevent protein fouling (by protein depositions) or sensor rejection by fibrotic capsule formation. The anti-fouling coating may be composed of one or more chemicals, including but not limited to, dextran, PEG, hyaluronic acid and/or chitosan. These compounds may be attached to the outside of the cellulose-based housing (e.g. hollow fibers) using divinylsulfone chemistry. To prevent sensor rejection by fibrotic capsule formation, the housing may be chemically modified with a layer(s) of tissue-specific signaling biomolecules (e.g. peptides, hormones, aptamers.) which promote cell-cell interaction and cell adhesion. The tissue-specific signaling biomolecules may be attached to the housing 14 by physiosorption or via chemical crosslinks to the sensor housing directly or the antifouling polymer layer. To prevent protein-adhesion and sensor rejection, a two layer a multi-component coating may be preferred. The first layer may be made of a single or a mixture of various anti-fouling polymers such as dextran, PEG, hyaluron acid or chitosan. The second component may be a tissue-compatible arsenal of aptamers specific to a variety of extracellular matrix proteins and integrin receptors, or RGD-type peptide which is able to recognize tissue-specific receptor sites. The RGD-type peptide may be fibronectin, laminin, vitronectin or a mixture thereof Immobilization of amino-terminated aptamers or RGD-type peptides may be facilitated by cross-linking to dextran with a bi-functional linker or by mild oxidation of dextran with periodate, followed by reductive amination of the Schiff's base between the peptide and dextran with sodium borohydride. Similar chemical strategies for covalent attachment of peptides may be utilized.

With reference to FIGS. 10A and 10B, while the use of two (or more) reporting moieties has been described in detail to address and/or compensate for variations in intervening skin optics other methods of analysis may be applied to extract the radiation converting efficiency of the first reporting moiety 24 (and hence e.g., glucose concentration). The skin or surrounding tissues may contain a third reporting moiety that would convert radiation provided by the radiation providing unit 28 into radiation which would "overlap" with at least a portion of the provided radiation, thereby creating interference. In this situation, it may be advantageous to employ a device and technique to discern, discriminate and/or reject that portion of the detected radiation not due to the analyte sensing device. In this regard, a number of methods for performing such rejection are known to those skilled in the art.

Such methods may include, for example, measurement of the conversion of radiation by skin or tissue alone, normalization of this conversion efficiency by some known quantity (for example, the intensity of radiation exiting the radiation providing unit), further normalization of the detected converted radiation from both skin and first and second reporting moieties together, and subsequent subtraction of the radiation converted by the skin. Other methods including multivariate regression analysis or principal component analysis, may also be implemented to discern, discriminate and/or reject that portion of the detected radiation not due to analyte sensing device (i.e., "isolate" contribution(s) from analyte sensing device).

Figure 11:
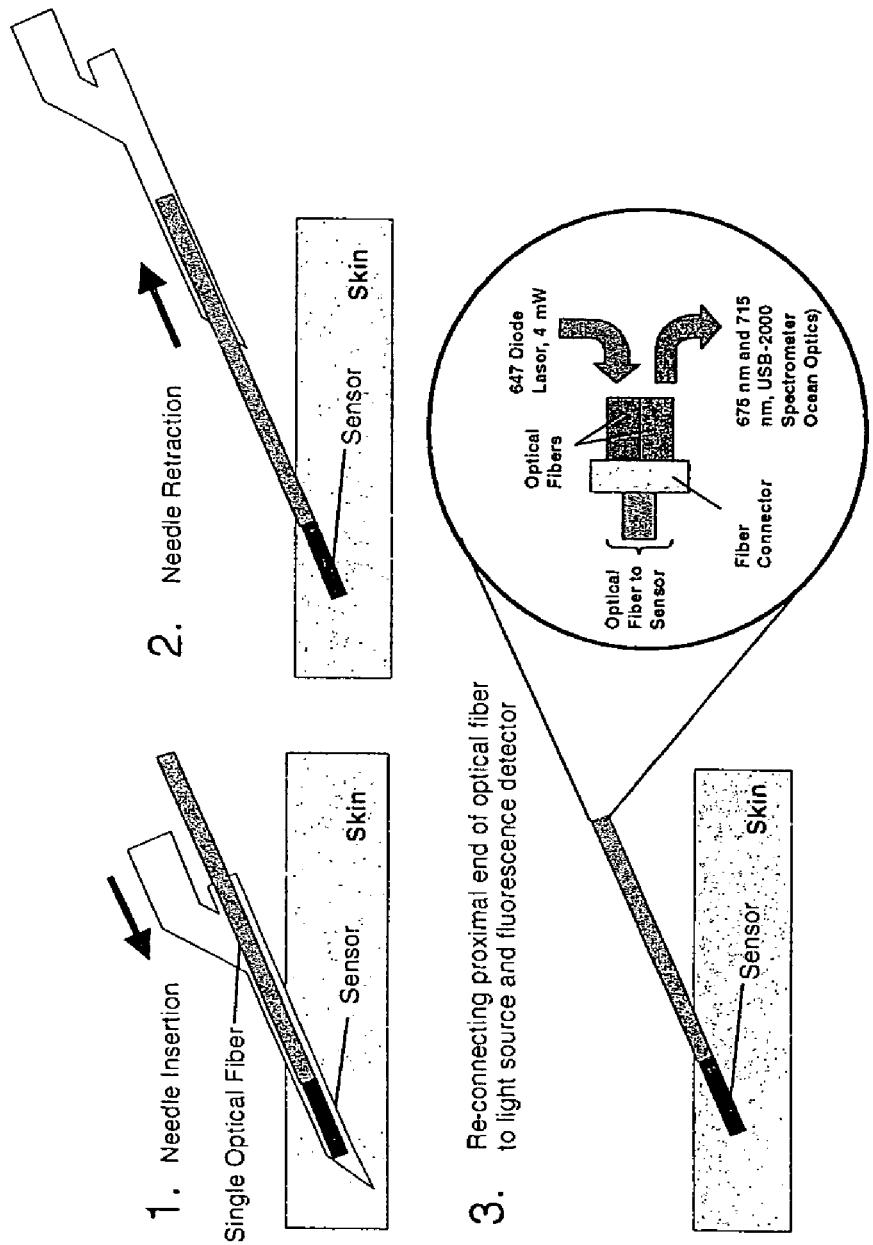
FIG. 11 is an illustration of an embodiment of the delivery and interrogation methods of the fiber-coupled sensor.
Figure 12:
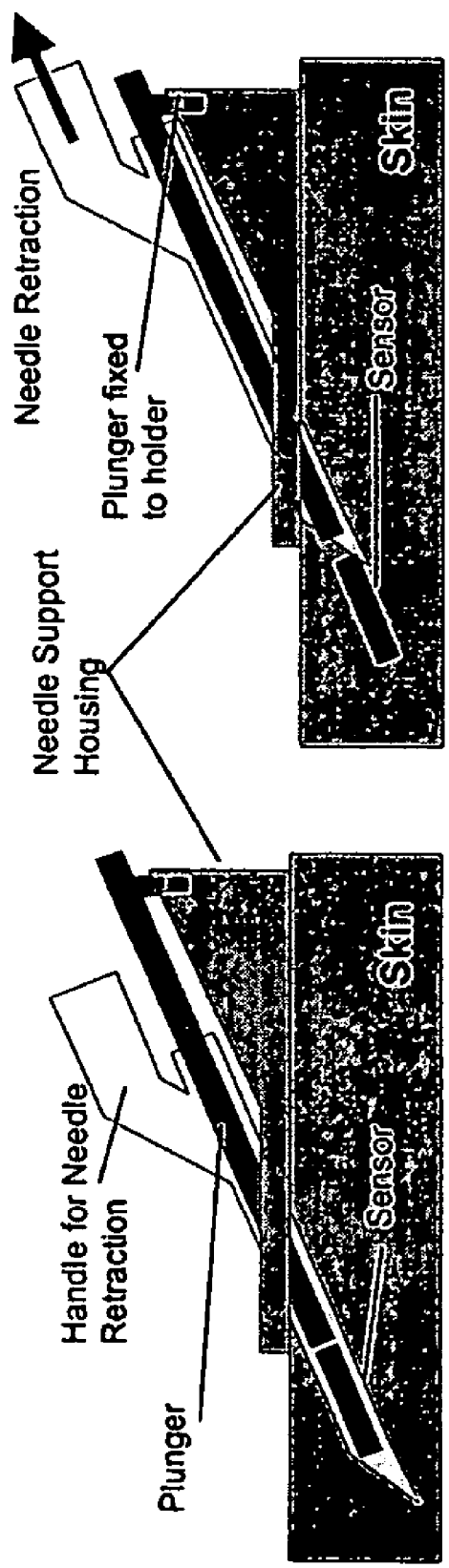
FIG. 12 shows the delivery integration a fully-implanted sensor.

With regard to FIGS. 11 and 12, when the analyte sensing device 10 may be contained in a hypodermic needle 86, the analyte sensing device 10 may be implanted into the skin tissue by pushing it through the hypodermic needle 86 inserted under the skin surface. When the analyte sensing device 10 includes a housing 14 of a polymer matrix, the external diameter of the particles may be made sufficiently small as to allow their injection. For example, one or a plurality of polymer spheres roughly 1-500 µm in diameter may be collected and injected into or underneath the skin or other desirable body location.

With reference to FIG. 12, one or more analyte sensing devices 10 may be inserted, implanted, disposed, placed and/or affixed by subcutaneous or intradermal injection. In this way, a number of locations of the body may be assessed and/or a gradient may be determined.

With reference to FIG. 12, the analyte sensing device 10 is implanted under the surface of the skin 40 of an animal. The analyte sensing device 10 may reside in a location in the tissue matrix where at least a portion of the sensing device 10 is in communication with blood or interstitial fluid. The analyte 52 of interest which is present in the surrounding body tissue, fluid, or matrix (e.g., interstitial fluid or blood) enters the device in amounts proportional to the concentration of the analyte in the surrounding body tissue fluid or matrix.

Plurality of Analyte Sensing Components

Figure 13:
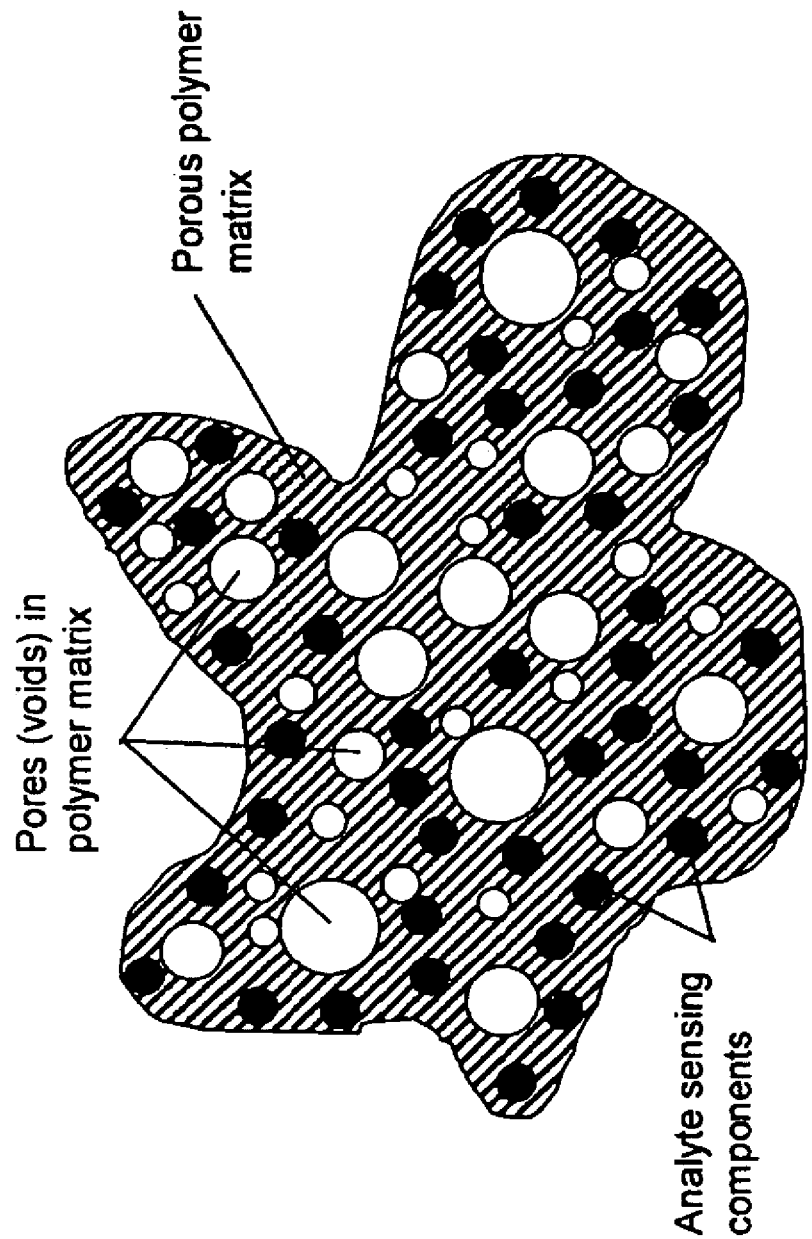
FIG. 13 illustrates yet another type of analyte sensing device.

With reference to FIG. 13, it may also be desirable to simultaneously or sequentially employ a plurality of analyte sensing components having the same or different analyte sensitivities. The sensitivity of the analyte sensing component 12 to the desired analyte 52 may be adjusted by altering the ratio of the analyte binding ligand sites to analyte analogue molecules 50 present in analyte sensing component 12. Such alterations may lead to sensor configurations which have optimized sensitivity over prescribed regions of analyte concentration.

With reference to FIG. 13, for example, a first analyte sensing component may be designed to be highly sensitive at low analyte concentrations, but its signal saturates at higher analyte concentrations. A second analyte sensing device, however, may be relatively insensitive at lower analyte concentrations, but may have a much larger dynamic range before saturation. Thus, these two complementary sensor formulations may be used in conjunction to accurately cover a larger range of analyte concentration values. The two devices may be discrete or may be formulated into a single, integrated sensing device.

With reference to FIG. 13, analyte sensing components 12 may be retained in the interior of polymeric housing 14 via covalent linkages to the polymeric backbone chains themselves. In this way, components of the analyte sensing components 12 would be "tethered" to the polymeric housing and free to move inside, but not to "escape". The analyte 52 would still be free to communicate in and out of polymeric housing 14 and to interact with the analyte sensing components 12.

EXAMPLES

The following examples are provided to more fully illustrate some of the embodiments of the present invention. It should be appreciated by those of skill in the art that the techniques disclosed in the examples which follow represent techniques discovered by the inventors to function well in the practice of the invention, and thus can be considered to constitute exemplary modes for its practice. However, those of skill in the art should, in light of the present disclosure, appreciate that many changes can be made in the specific embodiments that are disclosed and still obtain a like or similar result without departing from the spirit and scope of the invention.

Example 1

Immobilization of ConA to Sepharose

Dry powder of Sepharose pre-activated with CNBr was allowed to swell in cold 1 mM HCl for 30 minutes. Then, 10 mg/ml Concanavalin A was dissolved in 1 ml of 10 mM phosphate-buffered saline (PBS) and quickly added to the slurry of swollen CNBr-Sepharose. The slurry was gently rocked until the supernatant was free of ConA. ConA-Sepharose was then stored in PBS with 20% methanol until use. CNBr is exemplary of a linking molecule disposed between Concanavalin A and Sepharose.

Example 2

Shredding of ConA-Sepharose Beads

A suspension of ConA-Sepharose was washed in PBS. ConA-Sepharose was then shredded by stirring with a small magnetic stir bar on a stir plate for several days. Shredding was complete after no round beads were observed under microscope.

Example 3

Conjugation of Quencher Dye to Shredded ConA-Sepharose

Shredded beads were washed and the pH of the solution was equilibrated to 8.5 by the addition of a small aliquot of 0.5 M NaHCO$_3$. Cy7 or ALEXA® 750 succimidyl ester (0.4 mg) was dissolved in 100 µl DMSO. The dye solution was slowly added to the stirred bead suspension. The conjugation reaction was allowed to proceed for 60 minutes at room temperature. The blue-colored suspension was then washed with PBS until the supernatant was free of dye. The material was stored at 4° C. until use.

Example 4

Conjugation of Amino Dextran 70,000 with ALEXA® 647 Succinimidyl Ester

Approximately 10 mg of amino dextran 70,000 was dissolved in 1 ml of PBS and stirred with a micro-stir bar. The solution was centrifuged for 30 seconds at 10,000 g. ALEXA® 647 succinimidyl ester was dissolved in DMSO and added slowly to the stirred solution. The reaction was allowed to proceed for 60 min. The solution was passed through a Sephadex G50 size exclusion chromatography (SEC) column (20×0.75 cm). The conjugate was collected and stored at 4° C. until use.

Example 5

Conjugation of 2-deoxyglucose with ALEXA® 647 Dextran 70,000

ALEXA® 647 dextran was dialyzed twice against distilled water containing 0.9% NaCl for 24 hours. Then a solution of 1 M Na$_2$CO$_3$ was added to the stirred solution. A small amount of the bi-functional crosslinker divinyl sulfone (DVS) was added to the solution. The reaction was allowed to proceed for 45 to 60 min at room temperature, followed by addition of saturating amounts of 2-deoxyglucose (1 M). The reaction then was allowed to proceed overnight. Next, the solution was dialyzed extensively against 0.9% NaCl with 0.5% NaN$_3$, followed by PBS for 24 hours, The solution was stored at 4° C. until use.

Example 6

Preparation of Reference Dyes

TransFluoSpheres, with an optimal size between 150 to 250 microns were sonicated for 10 min to prevent hydrophobic, non-specific agglomeration of the reference beads. TransFluoSpheres were then mixed with 2% BSA (bovine serum albumin).

Example 7

Preparation of Assay Suspension

Shredded Cy7-ConA-Sepharose suspension (200 µl. supernatant/bead ratio of 1) was transferred into a 1.5 ml centrifuge tube. The suspension was centrifuged for 5 minutes at high speed. The supernatant was removed from the suspension with a pipette tip, and ALEXA® 647 dextran was added. The suspension was carefully mixed by gently aspirating it with a 200 µl pipette. After an incubation time of 15 to 20 min, the suspension was centrifuged at high speed. A small aliquot of supernatant was removed and TransFluoSpheres (0.2 microns) were added. The suspension was again carefully aspirated to ensure mixing of the sensor assay components. A fluorescence spectrum was acquired from the assay suspension to verify that the fluorescence intensity ratio at 675 nm and 715 nm was between 1 and 2. The sensor assay suspension was stored at 4° C. until use.

Example 8

Filling and Manufacturing of Hollow Fiber

Individual regenerated cellulose hollow fibers were filled with the sensor assay suspension. Short segments (0.5 to 1 cm in length) of the hollow fiber were homogenously filled with the blue-colored suspension, cut with scissors and sealed at the ends with cyanoacrylate. Sensors were stored in PBS at 4° C. until use.

Example 9

Heat-stability of Free and Immobilized Concanavalin A

The capability of various types of ConA to bind glucose was measured at various temperatures to determine the temperature-dependent rate of degradation. From these data, predictions were made about the stability of ConA at body temperature (37° C.) over time. Two different types of ConA in PBS buffer were tested: native ConA (3 mg/ml), and ConA-Sepharose (15 mg/ml ConA). The binding studies were done in a temperature controlled heat block. The rate loss of binding activity due to denaturation was measured after removal of the ConA derivative and reaction with dye-labeled dextran. The OD was measured and plotted vs. time to calculate the rate of degradation. After converting the degradation versus time into an Arrhenius plot, the degradation rate for 37° C. was extrapolated (Table II). Table II shows that ConA immobilized in Sepharose exhibits stability with a degradation rate of less than 0.1% per month, which translates into less than 1% per year. ConA immobilized to Sepharose is three orders of magnitude more stable than native ConA. Further, the presence of glucose in interstitial fluid has a favorable effect on the stability of the ConA, and, therefore, it is advantageous for ensuring a stable fluorescence sensor output.

TABLE II

Relative Rates (extrapolated) of Denaturation for Various Forms of ConA.

| | Extrapolated Relative Rate of Denaturation at 37° C. (% per month) | | |
|---|---|---|---|
| | 0 mM Glucose | 5 mM Glucose | Stability Factor |
| Native Con A | 160.0 | 32.0 | 1 |
| Sepharose Con A | 0.18 | 0.036 | 924 |

Example 10

Long-term Stability of in vitro Glucose Response of Fluorescence-based Affinity Sensors with Free and Immobilized ConA To demonstrate the improved stability of a fluorescence sensor composed of immobilized ConA over a sensor with free ConA, the response of the two different types of sensors were measured at body temperature (37° C.) over many weeks. The sensors included a glucose-permeable hollow, tubular housing (hollow fibers, outer diameter 220 microns, inner diameter 200 microns). The sensor with immobilized ConA contained a suspension of 70 kDa-dextran and shredded agarose-beads to which ConA was immobilized. To facilitate FRET, dextran was labeled with the donor dye ALEXA® 647 (Molecular Probes) and ConA-Sepharose was labeled with the modulating moiety Cy7 (Amersham). After the suspension was aspirated inside the hollow fibers, short segments were cut and sealed with a cyanoacrylate adhesive at both ends.

The sensor containing free ConA included Sephadex-beads (crosslinked dextran) and free ConA. Hollow fibers were filled with this suspension. To measure a fluorescence change when ConA is bound and free, Sephadex was dyed with Safranin O/Pararosanilin and ConA was labeled with ALEXA® 495 (Molecular Probes). When ConA was bound to Sephadex via glucose-residues, dyes effectively absorbed light and prevent the light from exciting the fluorescent dye ALEXA® 495. However, in the presence of glucose, ConA is displaced from the Sephadex beads and free to diffuse out of the beads into the area illuminated by the excitation light. This causes the fluorescence of ALEXA® 495 to increase. The increase in fluorescence correlates with increasing glucose concentrations.

Figure 14:
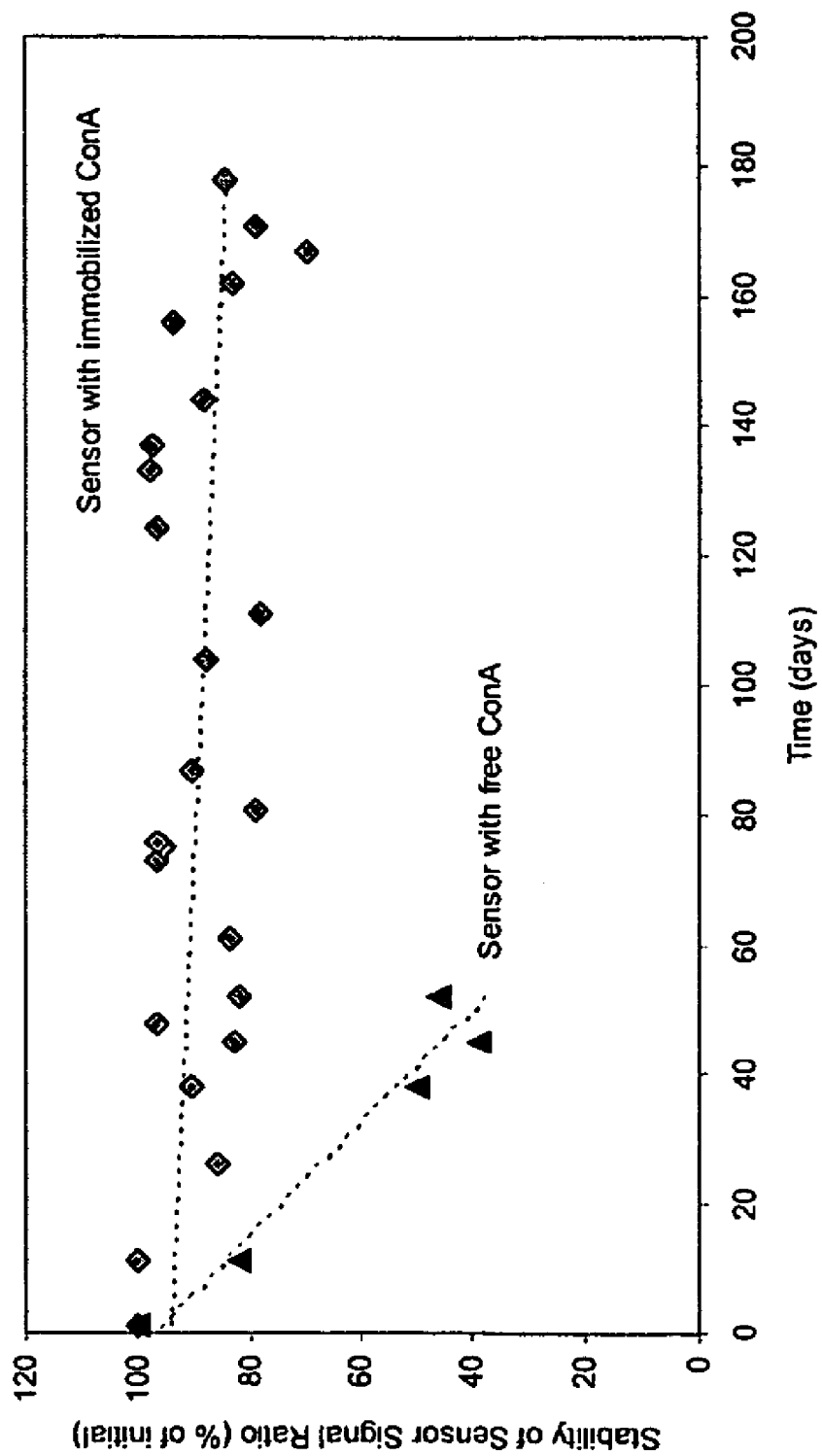
FIG. 14 is a graphic representation of comparative data over time of the relative stability of the glucose response of two sensing devices containing free and immobilized ConA.

Both sensors were then placed in a flow-through chamber set at 37° C. and their response to alternating glucose concentrations (between 0 and 20 mM) was continuously measured over time. The glucose-dependent fluorescence change relative to the first day was plotted over time. FIG. 14 shows that the sensor with immobilized ConA (diamonds line 78), remained relatively stable for up to 180 days, whereas the sensor with free ConA (triangles line 80), lost more than 60% of its initial fluorescence response after 40 days.

Example 11

Figure 15:
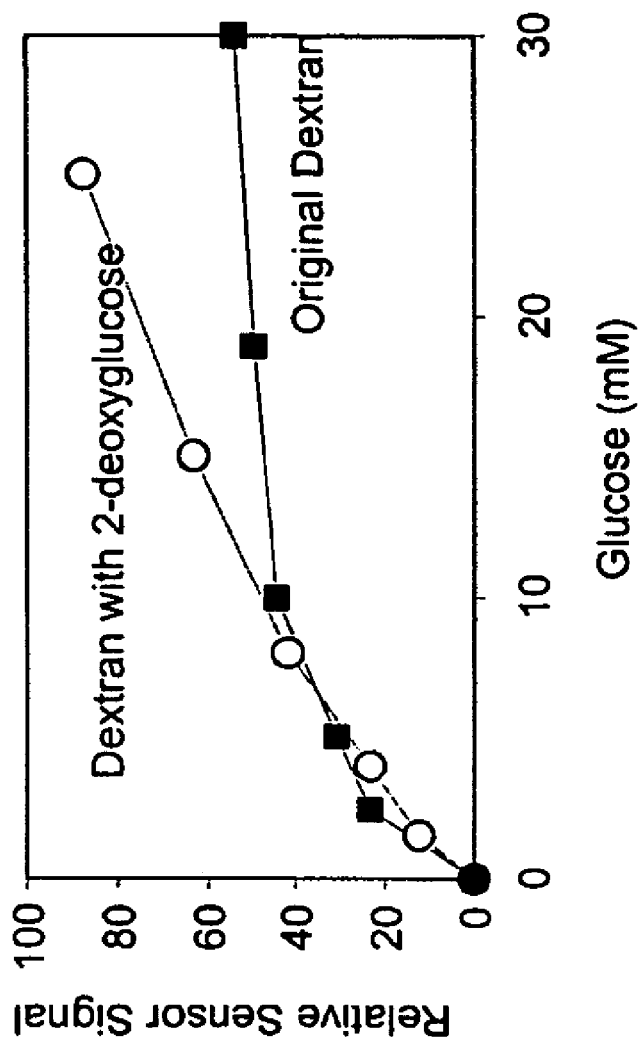
FIG. 15 is a graphic representation of glucose-calibration isotherms of two sensing devices for glucose; one containing non-modified dextran as glucose-analogue, and the other containing dextran modified with 2-deoxyglucose.

Extension of Glucose Concentration Range with Dextran Functionalized with 2-deoxyglucose to Cover Physiological Glucose Level Range The dynamic range of the sensor assay that includes Cy-7 ConA-agarose and dextran labeled with ALEXA® 647 is inadequate to encompass the entire glucose level ranging from 2.5 to 30 mM glucose. As can be seen in FIG. 15, when dextran alone (squares) is used the sensor signal levels off at approximately 10 to 15 mM glucose (line 84). At higher glucose concentrations, the sensor would not be functional. Therefore, in order to ensure that the sensor can measure glucose above 15 mM glucose, the dynamic range must be improved. This can be achieved by substituting alternative sugar moieties onto dextran by divinylsulphone via hydroxyl-groups at pH 14. After reaction of dextran with DVS for 1 or 2 hours, an excess amount (1 M) of the respective sugar is added to the solution. After 15 hours, the pH is changed to neutral and the solution is dialyzed overnight to remove non-reacted sugar. A variety of different sugars have been tested including maltose, 2-deoxyglucose, mannose, sucrose, and turanose. FIG. 14 shows the relative sensor signal for dextran and dextran modified with 2-deoxyglucose. Dextran modified with 2-deoxyglucose (circles) covered the physiological glucose concentration range (line 82). This is due to the higher affinity for 2-deoxyglucose than glucose for the binding sites of ConA and therefore a larger glucose concentration is required for dextran displacement.

Example 12

In Vivo Performance of Fiber-coupled and Fully Implanted Sensor in Rats

Figure 16:
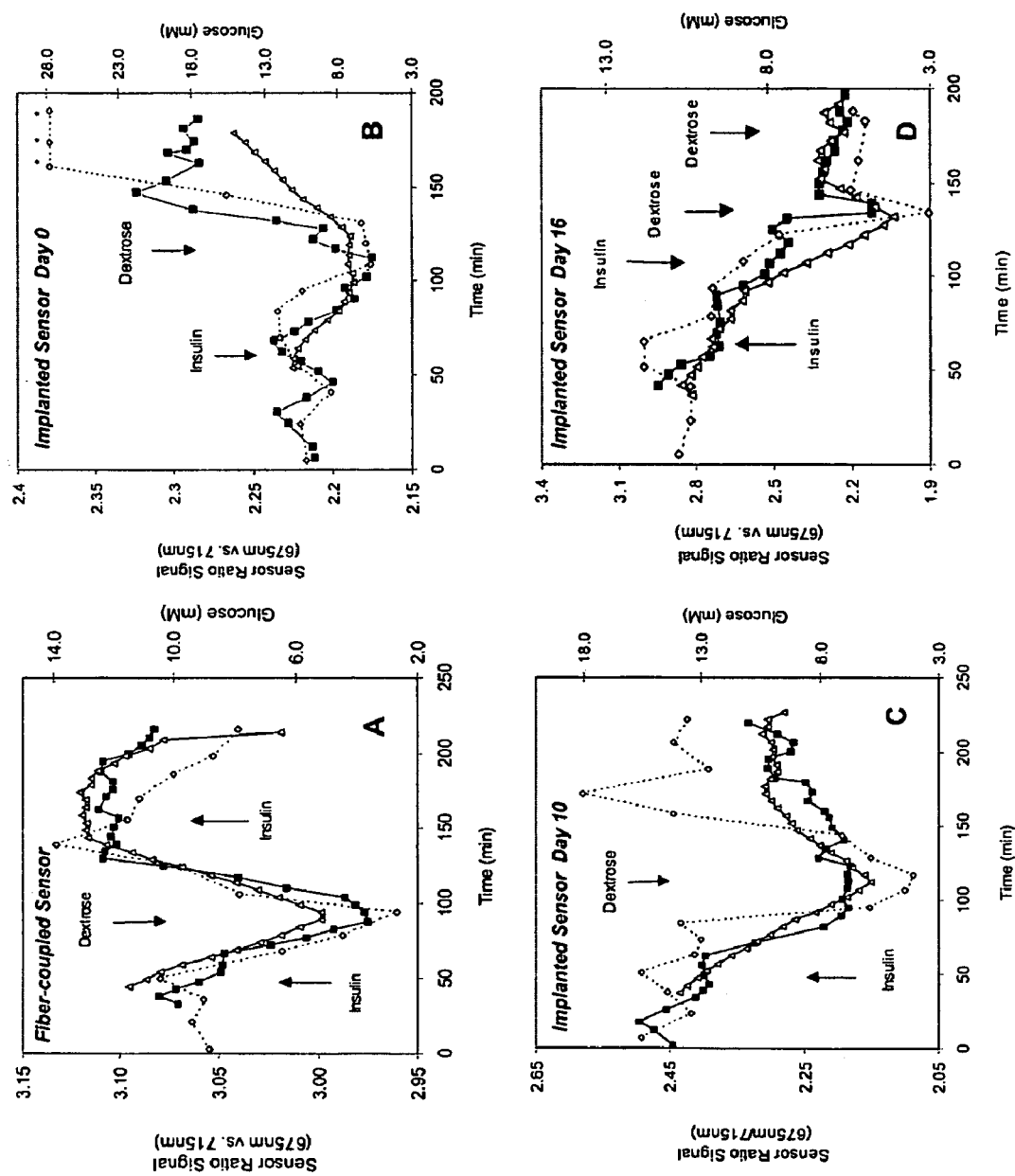
FIGS. 16A, 16B, 16C and 16D are graphic depictions of the in vivo performance of fiber coupled and fully implanted sensors in rats.

Acute and chronic in vivo evaluation of fiber-coupled and fully implanted sensors in rats was performed. FIGS. 11 and 12 depict the delivery of the fiber-coupled sensor and fully implanted sensor respectively. In FIG. 11, a single optical fiber 88, containing the sensor 10, was inserted under the skin 40 using a needle 86. The needle 86 was retracted. The proximal end of the single optical fiber 88 was connected to a light energy providing unit 28 and light energy detecting unit 30 via a fiber connector 122 and optical fibers 120. In FIG. 16, a needle 86 and plunger 92 were used to insert a sensor 10. The plunger 92 may be attached to a needle support housing 90.

Figure 17:
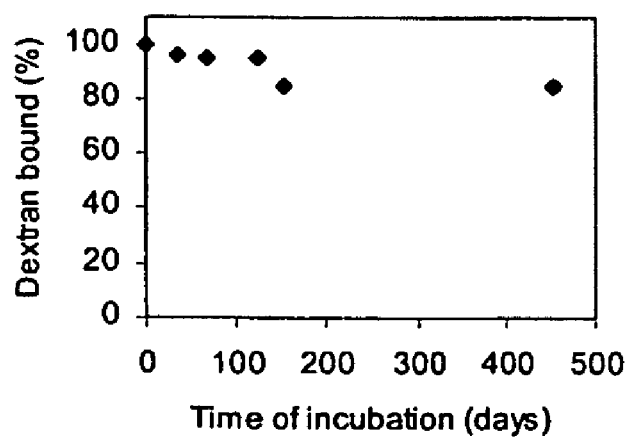
FIG. 17 is a graphic depiction of the fraction of fluorescein dextran bound to ConA over time.

FIG. 17A shows the response of the fiber-coupled sensor during a 3-hour experiment. The response of the transdermal sensor is shown at day 0 (FIG. 16B), day 10 (FIG. 16C), and day 16 (FIG. 16D). Open squares (□) indicate a FRET-sensor, (lines 94, 102, 108 and 114), open triangles (Δ) indicate a Minimed/Metronics CGMS sensor (lines 96, 104, 110 and 112), open diamonds (◇) indicate blood glucose (lines 98, 100, 106 and 116). Data points denoted with * indicates that the blood glucose values measured with a glucose meter were out-of-range. Arrows indicate addition of insulin and dextrose. Insulin and dextrose was administrated to simulate decrease and increase in blood glucose levels, respectively, in order to determine how well the implanted glucose sensor is capable of tracking changes in blood glucose levels.

Experiments demonstrating improved stability of non-labeled Sepharose-immobilized ConA and proof-of-concept assays pertaining to measuring glucose-dependent fluorescence changes in sensors with untagged ConA-Sepharose Example 13

Retention of Binding Activity of Sepharose-immobilized ConA at 37° C. Over 450 Days A suspension (500 μl) of ConA-Sepharose in phosphate buffer saline (pH 7) was incubated in several 1.5 ml tubes at 37° C. To determine the functional binding activity of the Sepharose-immobilized ConA, two tubes were removed from the incubator at different times, and a binding assay was performed. This was done by gently mixing the ConA-Sepharose suspension with 500 μl of fluorescein-dextran for 15 min. Then, the amount of free fluorescein-dextran in the supernatant was measured. From the amount of measured free fluorescein dextran, the fraction of bound fluorescein dextran was calculated and plotted over time (see FIG. 17). The data show that even after 450 days, 85% of the fluorescein dextran was still bound to ConA-Sepharose, indicating minimal loss of ConA-binding activity of only 15% over the same period.

Example 14

Figure 18:
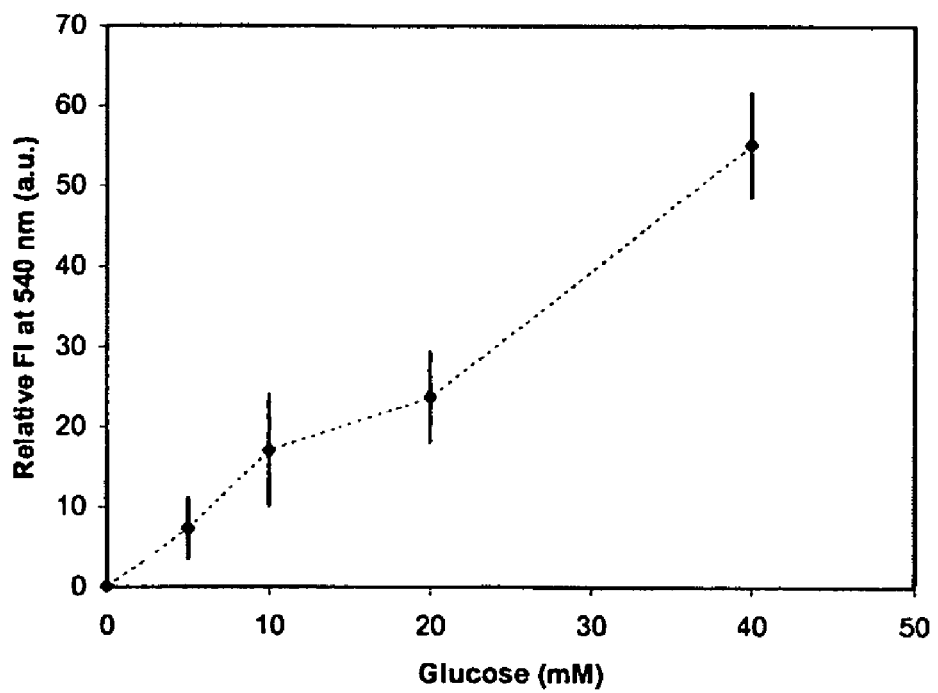
FIG. 18 is a graphic depiction of the dependence of fluorescence on glucose concentration in a sensor suspension.

Demonstration of Glucose-dependent Change in Fluorescence in a Sensor Suspension Composed of Untagged ConA-Sepharose In order to demonstrate utilizing the superior stability of untagged ConA-Sepharose for quantifying glucose concentration in a fluorescence sensor, ConA-Sepharose was mixed with 70,000 rhodamin dextran and an aliquot of small polystyrene particles (approximately 1-20 microns) containing quantum dots (QD, excitation 513 nm, emission 540 nm). The absorbance spectrum of rhodamin (540 nm) significantly overlapped with the fluorescence spectrum of the QDs. This suspension was then transferred into different tubes to which various amounts of glucose were added, resulting in final glucose concentrations of 0, 5, 10, 20 and 40 mM. The sensor suspension was then mixed and incubated for 30 minutes. Then, the fluorescence in the settled bead portion of the suspension was measured at 540 nm with a Perkin Elmer fluorescence spectrophotometer. The average fluorescence (triplicates) was plotted against the glucose concentration. The graph in FIG. 18 shows an increase in fluorescence of the sensor suspension, as expected, with increasing glucose concentrations. The mechanism of the fluorescence increase can be explained by the difference in spatial concentration of rhodamin-dextran when bound to Sepharose-particles in the absence of glucose, and when it is dispersed in the presence of glucose. In the absence of glucose, the fluorescence is lower due to strong absorption of the fluorescence by the bound rhodamin dextran. However, in the presence of glucose the fluorescence was less absorbed when the rhodamin dextran was displaced from the beads, lowering the local concentration of rhodamine inside the beads. To illustrate it more clearly, in the absence of glucose the sensor suspension is less transparent for the fluorescence of the QDs than in the presence of glucose. In summary, this experiment shows that untagged ConA-Sepharose can be used for glucose-specific fluorescence measurement to implement a sensor device which remains functional for more than a year.

Example 15

Demonstration of Another Example of How to Use Untagged ConA-Sepharose

Figure 19:
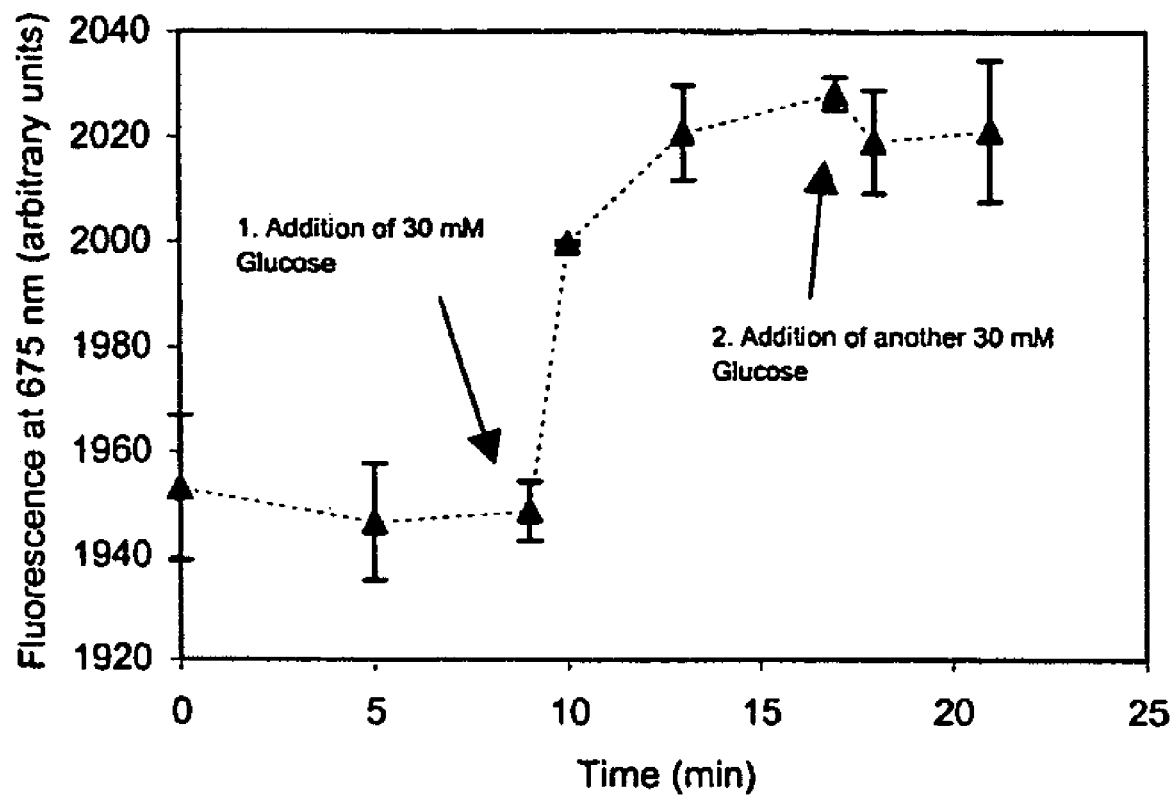
FIG. 19 is a graphic representation of the response of fluorescence to the addition of glucose to a sensor.

We employed a dye-carrying entity to measure glucose-dependent fluorescence changes. First, Alexa 750 (Invitrogen) was conjugated to bovine serum albumin (BSA), the dye carrying entity. Then, Alexa 750-BSA conjugate and ConA were co-immobilized to cyanogen bromide-activated Sepharose 4 Fast Flow (Amersham Bioscience), resulting in an arrangement in which immobilized ConA is closely located to immobilized Alexa 750 BSA. The Alexa 750 BSA/ConA-Sepharose bead suspension was then mixed with Alexa 647 dextran, the glucose-analogue. A small aliquot of the sensor suspension was then continuously stirred on a magnetic stirrer to improved mass convection. The baseline fluorescence of the stirred sensor suspension was monitored with an optical fiber connected to a small USB-powered spectrophotometer (Ocean Optics 2000). After approximately 10 min, glucose with a final concentration of 30 mM was added and the rise in fluorescence monitored. After 18 minutes another aliquot of glucose solution (final concentration 60 mM) was added. FIG. 19 shows a significant increase of the fluorescence after the first addition of glucose by approximately 80 arbitrary units (triplicates). The absence of a further rise in fluorescence after the second addition of glucose indicates saturation of the assay chemistry with glucose which is characteristic for the ConA-Sepharose system. The effect can be explained by considering that in the absence of glucose, Alexa 647 dextran is bound to Sepharose-immobilized ConA, which is in close proximity to a quencher dye (modulating entity) tagged to BSA, resulting in FRET-typical fluorescence quenching of Alexa 647 (first reporting entity) by Alexa 750. However, in the presence of glucose, dextran is displaced from the binding sites of ConA, resulting to an increase in spatial distance of both dyes, followed by an increase in fluorescence of Alexa 647. Overall, the experiment demonstrates another example of how to employ untagged ConA-Sepharose for the implementation of a long-term stable fluorescence sensor for glucose detection.

What is claimed is:

1. An analyte sensing device, comprising:
   a housing; and
   a composition located within the housing, said composition comprising:
      a matrix consisting of a plurality of macroporous particles or beads;
      at least one lectin derivatized to said macroporous particles or beads for thermodynamically stabilizing a functional binding activity, said at least one lectin having a binding specificity for glucose;

an analyte analog capable of being bound by the at least one lectin;

a first reporting moiety having a spectral response intensity substantially dependent upon the concentration of glucose within the housing; and a first modulating moiety adapted for influencing the intensity of the spectral response;

wherein said particles or beads have lumens with an exclusion volume larger than the molecular weight of said at least one lectin and said analyte analog.

2. The analyte sensing device of claim 1, wherein the first reporting moiety comprises a fluorescent dye.

3. The analyte sensing device of claim 1, wherein the first modulating moiety comprises a fluorescent dye bound to a dye-carrying entity immobilized to a support matrix.

4. The analyte sensing device of claim 3 wherein said dye-carrying entity is conjugated to a support matrix.

5. The analyte sensing device of claim 1, wherein the analyte analog comprises dextran modified with a modifier selected from the group consisting of glucose-specific saccharides, mannose specific-saccharides, mannose, lactose, 2-deoxyglucose, and combinations thereof.

6. The analyte sensing device of claim 1, wherein the analyte sensing device further comprises a second reporting moiety whose intensity of spectral response is substantially independent of the concentration of glucose within the housing.

7. The analyte sensing device of claim 6, wherein the second reporting moiety comprises a fluorescent organic dye, a fluorescent nanoparticle or a polymer crosslinked dye.

8. The analyte sensing device of claim 6, wherein a common moiety acts as a modulating moiety and a second reporting moiety.

9. The analyte sensing device of claim 1, wherein the housing comprises a hollow fiber of regenerated cellulose.

10. The analyte sensing device of claim 1 wherein said lectin is derivatized by a molecular entity comprising a chemical linker between said lectin and said matrix.

11. The analyte sensing device of claim 1 wherein said housing comprises a permeable or semipermeable portion.

12. The analyte sensing device of claim 1 wherein said first reporting moiety is attached to the analyte analog.

13. The analyte sensing device of claim 6, wherein the second reporting moiety is selected from the group consisting of TransfluoSpheres, quantum dots, Alexa 700, and Alexa 750.

14. The analyte sensing device of claim 5, wherein the molecular weight of dextran is between about 30 and about 130 kDa.

15. The analyte sensing device of claim 5, wherein the molecular weight of dextran is about 70 kDa.

16. The analyte sensing device of claim 1, wherein the first reporting moiety comprises Alexa 647 and the modulating moiety is selected from the group consisting of Cy7, Alexa 680, and QSY21.

17. The analyte sensing device of claim 6 wherein said second reporting moiety is embedded inside nanoparticles comprising polystyrene, polycarbonate, or PMMA.

18. The analyte sensing device of claim 6, wherein the flurescence wavelength of the second reporting moiety is between about 600 nm and about 800 nm.

19. An analyte sensing device, comprising:
a housing; and
a composition located within the housing, said composition comprising:

at least one lectin having a binding activity, an analyte analog capable of being bound by the at least one lectin;

a first reporting moiety having a spectral response intensity substantially dependent upon the concentration of glucose within the housing;

a first modulating moiety adapted for influencing the intensity of the spectral response; and a matrix consisting essentially of a plurality of macroporous particles or beads having lumens, said particles or beads being in a fixed relationship to said at least one lectin for stabilizing said binding activity;

wherein said plurality of macroporous particles or beads allow free diffusion of an analyte and of said analyte analog into and out of said lumens.

20. The analyte sensing device of claim 19 wherein the first reporting moiety comprises a fluorescent dye.

21. The analyte sensing device of claim 19, wherein the first modulating moiety comprises a fluorescent dye bound to a dye-carrying entity immobilized to a support matrix.

22. The analyte sensing system of claim 21 wherein said dye-carrying entity is conjugated to a support matrix.

23. The analyte sensing device of claim 19, wherein the spectral response comprises fluorescence.

24. The analyte sensing device of claim 19 wherein said analyte analog comprises dextran modified with a modifier selected from the group consisting of glucose-specific saccharides, mannose specific-saccharides, mannose, lactose, 2-deoxyglucose, and combinations thereof.

25. The an analyte sensing device of claim 23 wherein said fluorescence is at a wavelength of between about 600 nm and about 800 nm.

26. The analyte sensing device of claim 19 wherein the housing comprises a hollow fiber of regenerated cellulose.

27. The analyte sensing device of claim 19 further comprising a second reporting moiety whose intensity of spectral response is substantially independent of the concentration of glucose within the housing.

28. The analyte sensing device of claim 27 wherein said second reporting moiety is incorporated into macroporous beads by physiosorption or covalent chemical attachment.

29. The analyte sensing device of claim 27 wherein said second reporting moiety is embedded inside nanoparticles comprising polystyrene, polycarbonate, or PMMA.

30. The analyte sensing device of claim 19 wherein said housing comprises a permeable or semipermeable portion.

31. The analyte sensing device of claim 19 wherein said first reporting moiety is attached to the analyte analog.

32. The analyte sensing device of claim 19 wherein a common moiety acts as a modulating moiety and a second reporting moiety.

33. An analyte sensing device comprising
a housing; and
an analyte sensing composition located within the housing, said composition comprising:

a matrix consisting essentially of a plurality of macroporous particles or beads substantially evenly distributed throughout said housing;

at least one lectin derivatized to said macroporous particles or beads for thermodynamically stabilizing a functional binding activity;

a first reporting moiety having a spectral response intensity substantially dependent upon the concentration of an analyte within the housing; and a first modulating moiety adapted for influencing the intensity of the spectral response.

34. The analyte sensing device of claim 33 wherein the at least one reporting moiety comprises a fluorescent dye.

35. The analyte sensing device of claim 33 wherein said at least one modulating moiety has a fluorescent emission spectrum that overlaps an absorption spectrum of said at least one reporting moiety.

36. The analyte sensing device of claim 33 wherein said housing comprises a permeable or semipermeable portion.

37. The analyte sensing device of claim 33 wherein said at least one modulating moiety comprises a fluorescent particle bound to a dye-carrying entity immobilized to a support matrix.

38. The analyte sensing device of claim 33 wherein said at least one modulating moiety comprises a fluorescent nanoparticle.

39. The analyte sensing device of claim 33 further comprising an analyte analog capable of being bound by the at least one lectin.

40. The analyte sensing device of claim 33 further comprising an analyte analog capable of being bound by concanavalin A.

41. The analyte sensing device of claim 39 wherein the analyte analog comprises dextran modified with a modifier selected from the group consisting of glucose-specific saccharides, mannose specific-saccharides, mannose, lactose, 2-deoxyglucose, and combinations thereof.

42. The analyte sensing device of claim 33 further comprising a second reporting moiety whose intensity of spectral response is substantially independent of the concentration of analyte within the housing.

43. The analyte sensing device of claim 42 wherein said second reporting moiety is embedded inside nanoparticles comprising polystyrene, polycarbonate, or PMMA.

44. The analyte sensing device of claim 40 wherein said concanavalin A is derivatized by a chemical linker between concanavalin A and said matrix.

45. The analyte sensing system of claim 33, wherein said at least one modulating moiety also acts as a second reporting moiety.

46. The analyte sensing device of claim 33 wherein said composition comprises first and second reporting moieties, said second reporting moiety comprises a fluorescent organic dye, a fluorescent nanoparticle or a polymer crosslinked dye.

47. The analyte sensing device of claim 33 wherein said composition comprises first and second reporting moieties, said second reporting moiety is capable of converting optical radiation between 630 and 650 nm into optical radiation between 650 and 850 nm.

48. The analyte sensing device of claim 42 wherein said second reporting moiety is incorporated into macroporous beads by physiosorption or covalent chemical attachment.

49. The analyte sensing device of claim 42 wherein said second reporting moiety is embedded inside nanoparticles comprising polystyrene, polycarbonate, or PMMA.

50. The analyte sensing device of claim 46 wherein said nanoparticles are coated on their surfaces with chemicals by physiosorption or by covalent chemical attachment.

51. The analyte sensing device of claim 1, wherein said housing is at least 50% packed with said particles or beads.

* * * * *